United States Patent [19]

Doyama et al.

[11] Patent Number: 5,555,894
[45] Date of Patent: Sep. 17, 1996

[54] FORCE SENSATION EXHIBITING DEVICE, DATA INPUT DEVICE AND DATA INPUT EQUIPMENT

[75] Inventors: Yoshiaki Doyama, Hirakata; Masataka Ozeki, Osaka; Keizo Matsui, Kobe; Yoshiteru Ito, Takatsuki, all of Japan

[73] Assignee: Matsushita Electric Industrial Co., Ltd., Osaka, Japan

[21] Appl. No.: 235,948

[22] Filed: May 2, 1994

[30] Foreign Application Priority Data

| May 11, 1993 | [JP] | Japan | 5-109529 |
| Sep. 28, 1993 | [JP] | Japan | 5-241715 |
| Dec. 28, 1993 | [JP] | Japan | 5-336976 |

[51] Int. Cl.$^6$ .................................................. A61B 5/103
[52] U.S. Cl. .................................................. 128/782
[58] Field of Search ................................ 128/739, 774, 128/782; 33/511, 512; 73/865.4

[56] References Cited

U.S. PATENT DOCUMENTS

| 4,414,984 | 11/1983 | Zarudiansky | 128/774 |
| 4,949,729 | 8/1990 | Haski | 128/782 |
| 4,986,280 | 1/1991 | Marcus et al. | 128/782 |
| 5,329,813 | 7/1994 | Lewis | 128/774 |
| 5,381,805 | 1/1995 | Tuckett et al. | 128/739 |

FOREIGN PATENT DOCUMENTS

| 1175432 | 8/1985 | U.S.S.R. | 128/774 |

*Primary Examiner*—Max Hindenburg
*Attorney, Agent, or Firm*—Beveridge, DeGrandi, Weilacher & Young, LLP

[57] ABSTRACT

A data input device includes a housing which can be grasped by a hand. The housing is equipped with a detecting device that detects a displacement or pressure at a portion of the housing on which fingers are placed when the housing is grasped by the hand. The data input device may include plural sensors to detect displacement or pressure at several different finger belly portions of the fingers. Also, plural sensors may be provided for each finger belly portion. The data input device may be used to control the movement of remotely located mechanical fingers or virtual fingers shown on a display.

20 Claims, 37 Drawing Sheets

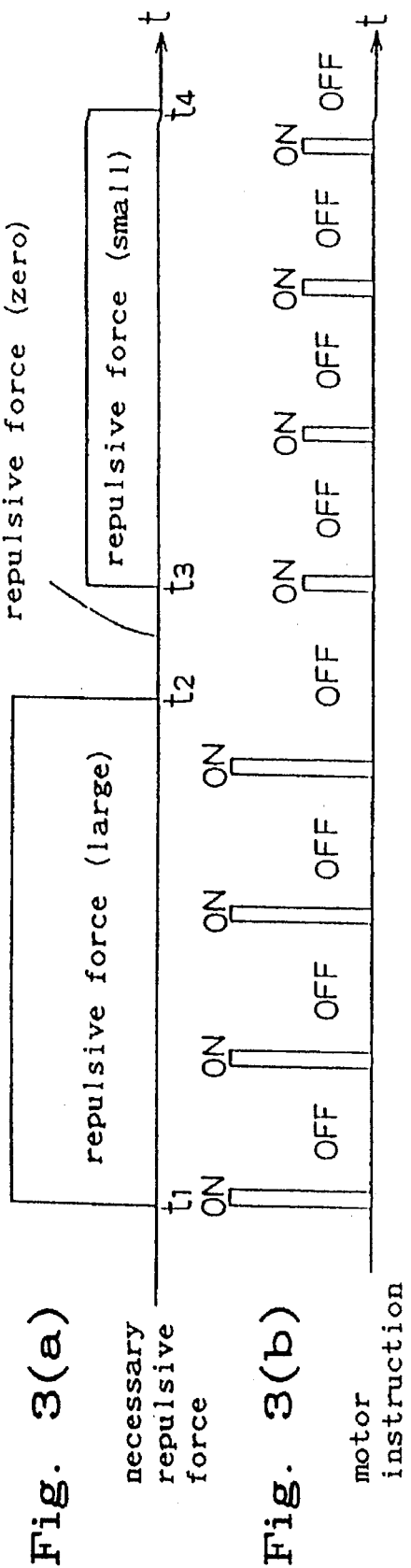
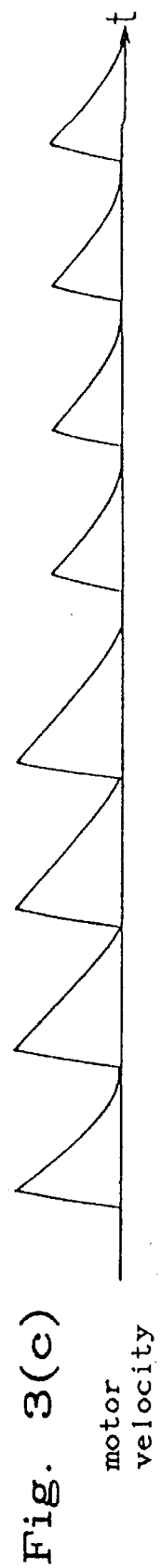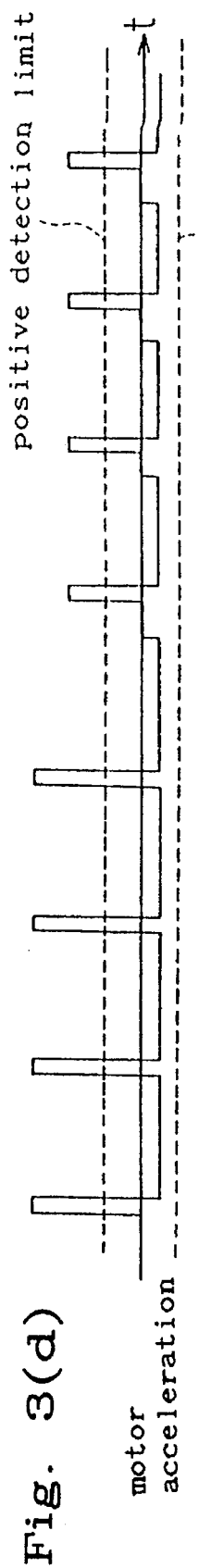
Fig. 3(a), Fig. 3(b), Fig. 3(c), Fig. 3(d)

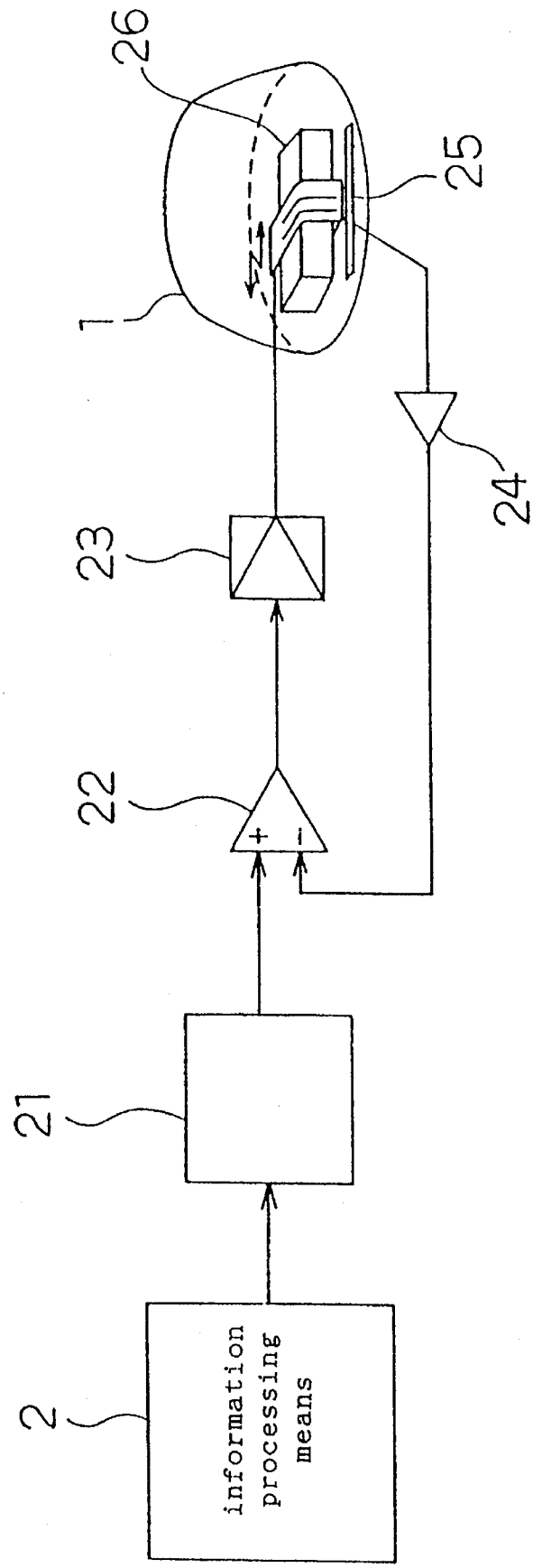

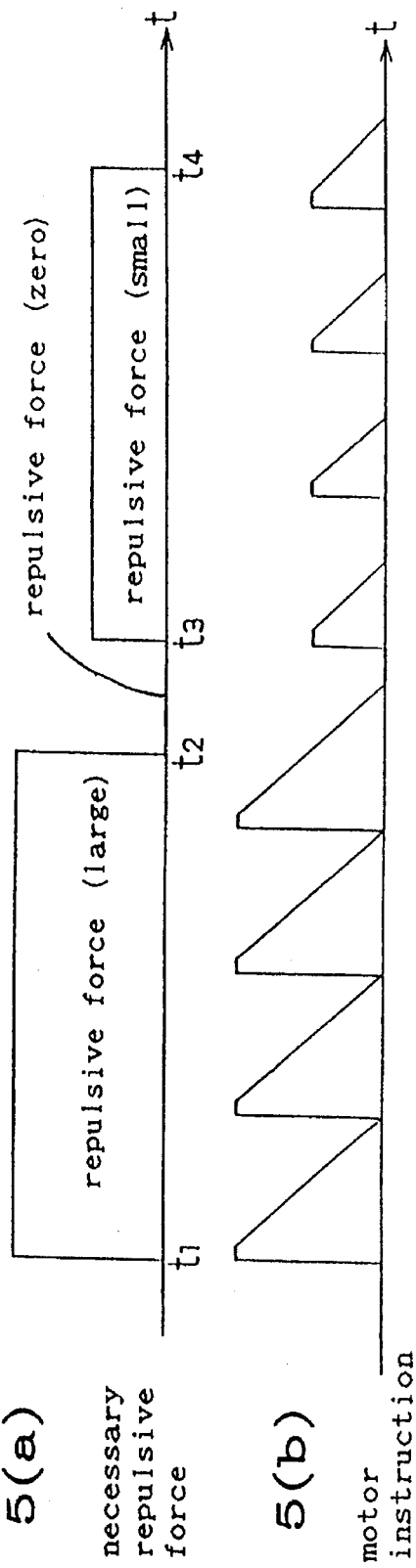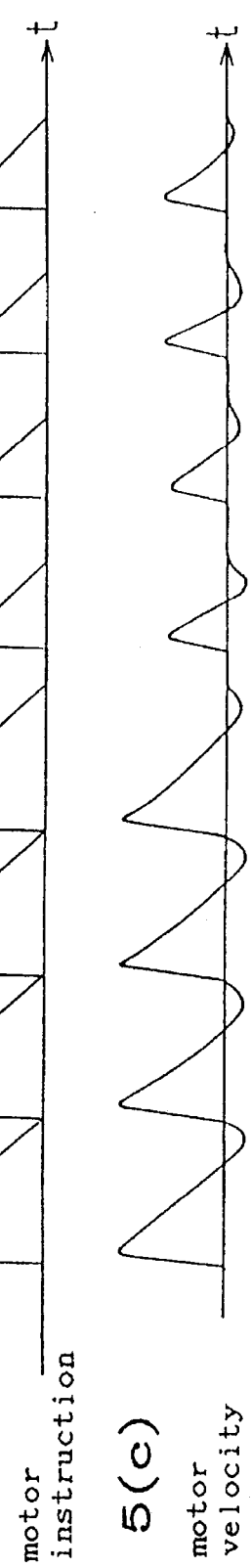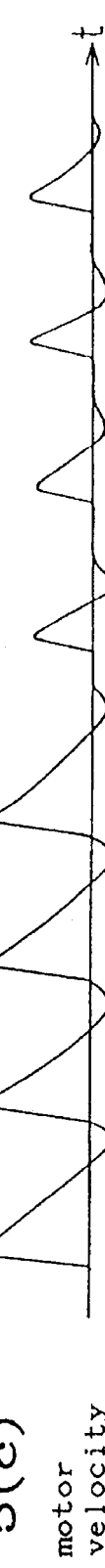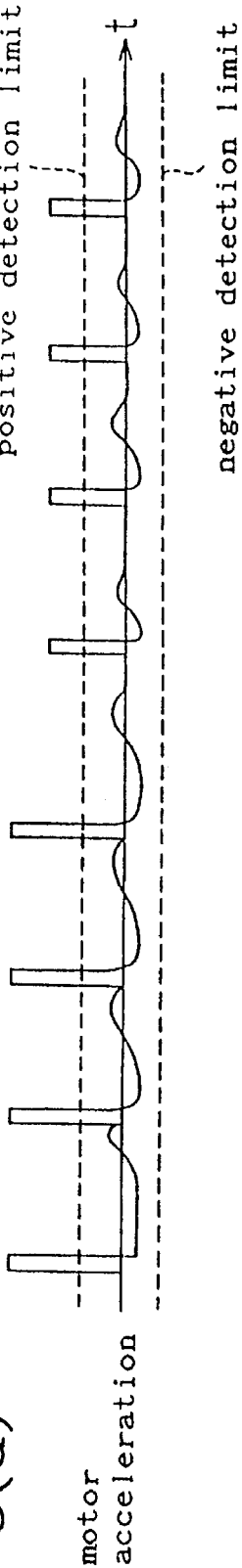

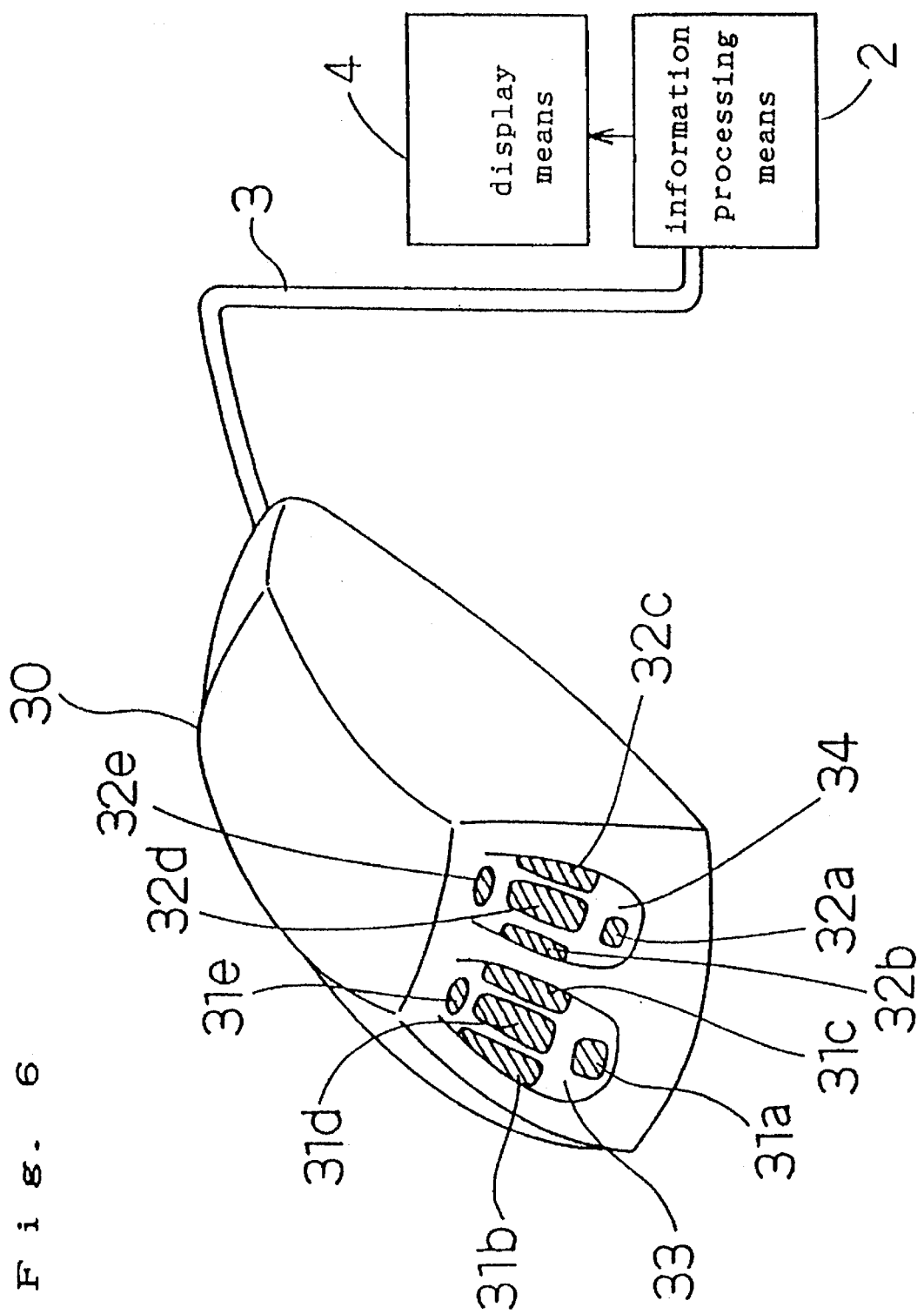

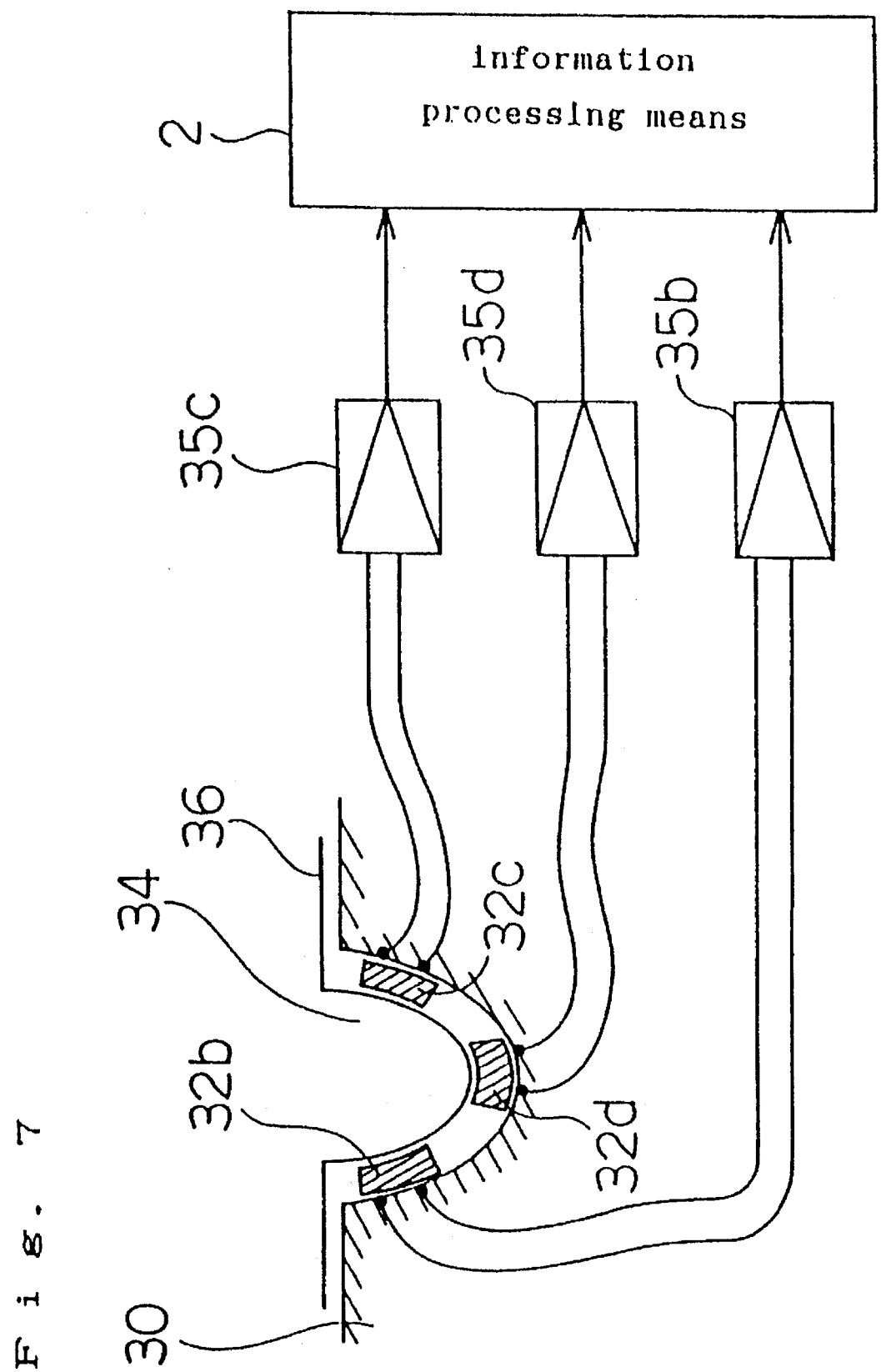

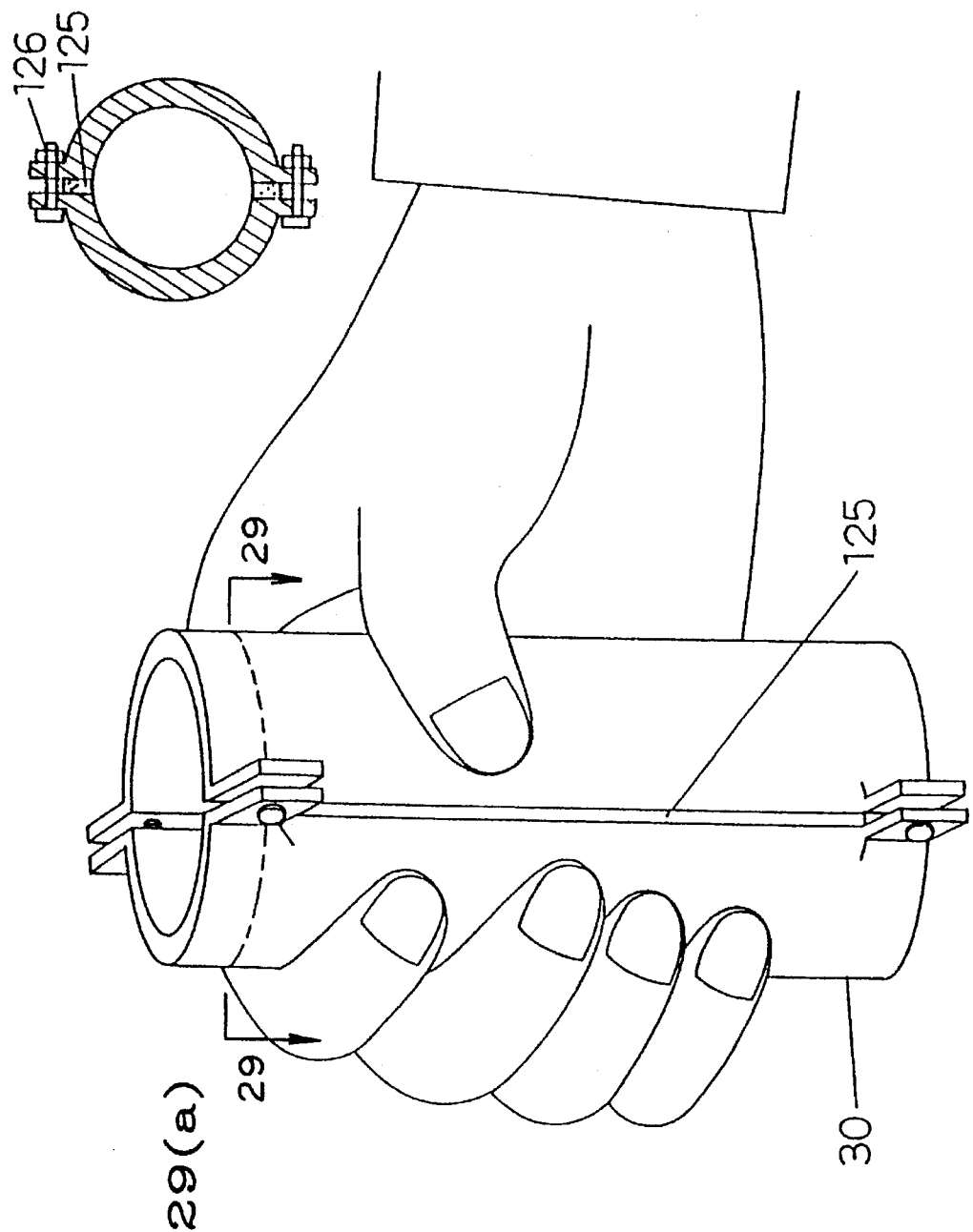

Fig. 42(a)
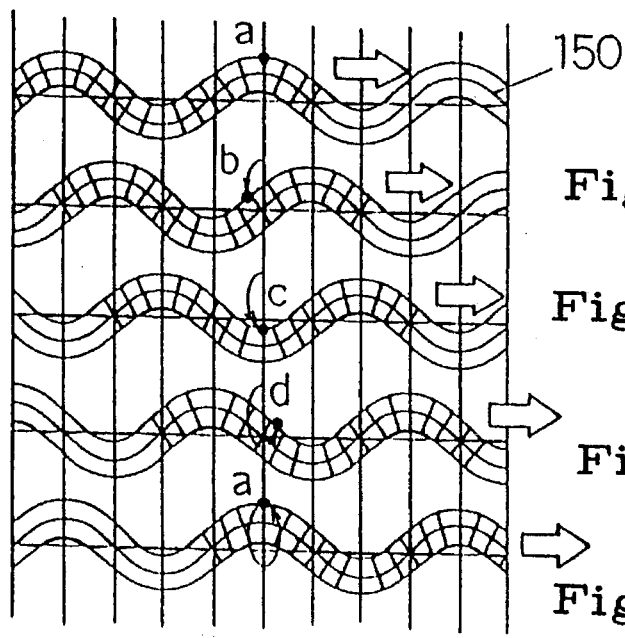
Fig. 42(b)
Fig. 42(c)
Fig. 42(d)
Fig. 42(e)
⇨ moving direction of advancing wave
Fig. 43
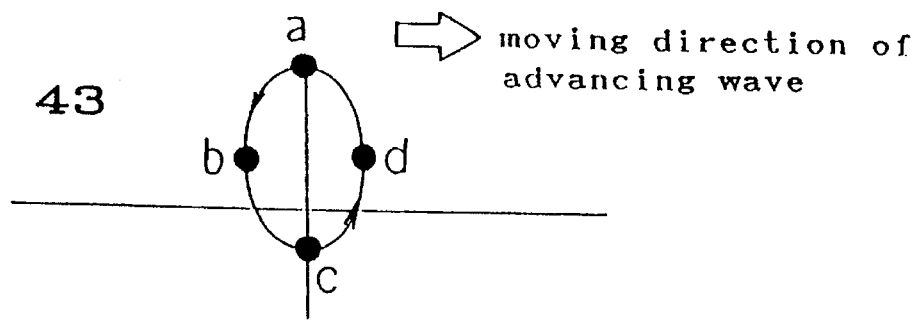
Fig. 44
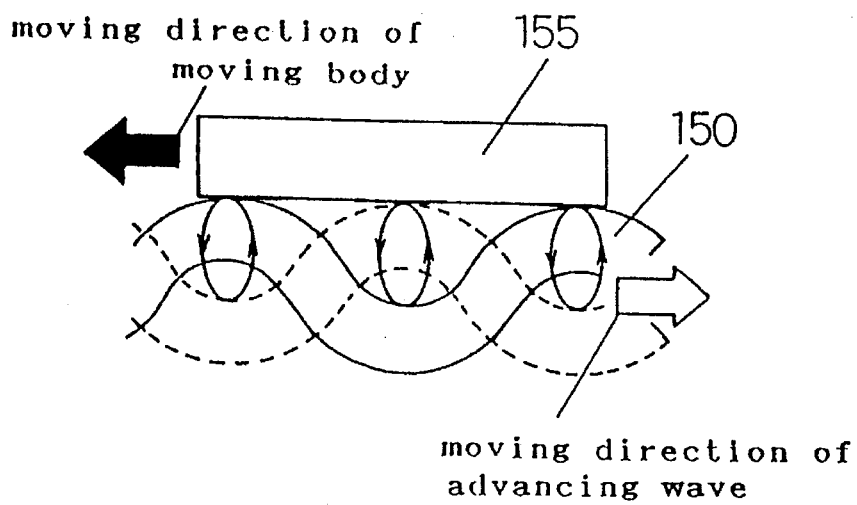
moving direction of moving body
moving direction of advancing wave

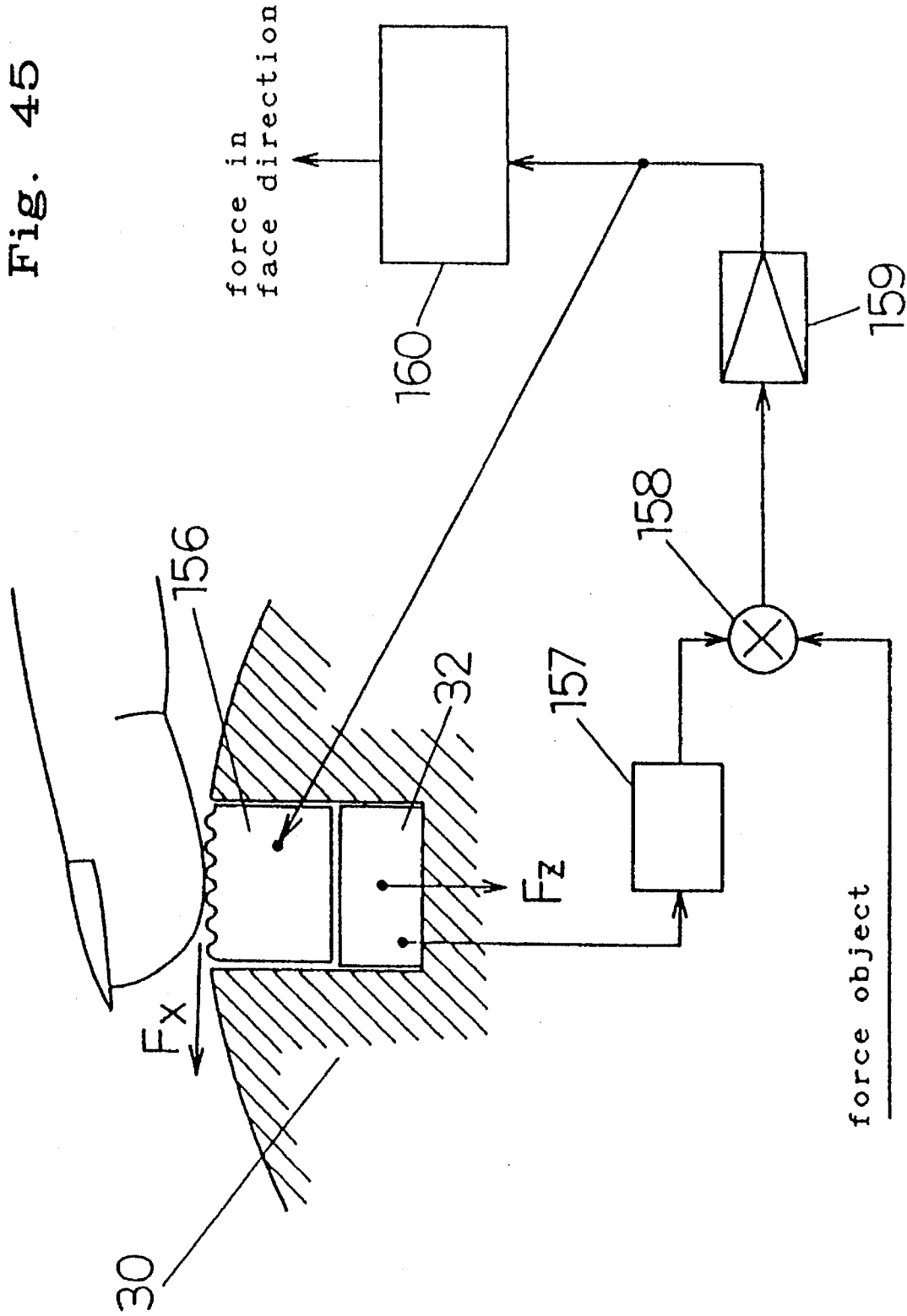

FORCE SENSATION EXHIBITING DEVICE, DATA INPUT DEVICE AND DATA INPUT EQUIPMENT

DETAILED DESCRIPTION OF THE INVENTION

1. Field of the Invention

The present invention relates to a force sensation exhibiting device, a data input device and data input equipment which are applicable to a device which makes an operator feel as if a virtual object as data within a calculator is actually present, to make a modeling operation done in the computer and to experience preliminarily how to use the product without manufacturing a prototype, or to a device wherein the operator can operate the object in a remote area while feeling as if it is in hand.

2. Related Art

FIG. 13 is a view showing the structure of a conventional simulator by means of an input method using the fingers and an image display device. This is to experience preliminarily how to use a device by operating an object which does not actually exist using the fingers, The operator 120 is equipped with a system glove 110 for inputting information so that the machine can read the positional data of the fingers. As the system glove 110 for inputting the information, there can be mentioned a data glove of V.P.L. Research Co. in the U.S.A. (hereinafter referred to as "VPL Co."). The data glove of VPL Co. detects the bending angle of the fingers by sewing an optical fiber on a thin glove to utilize the change of the light transmittance of the optical fiber by the bending of the optical fiber caused by bending the fingers. The thus obtained mechanical positional data of the fingers is sent to the contacting force-sensing type calculating means 112 in the information processing means 2. The contacting force-sensing type calculating means 112 calculates the shape data 115 of the virtual object and the input positions of the fingers input to calculate the positional relations between the fingers and the object. For example, when the fingers are on the surface or minutely inside the surface of the virtual object, this is when the fingers touch the virtual object. And when there are more than two faces to be touched, it is possible to operate to lift the virtual object. The obtained positional relations of the virtual object and the hand and fingers are displayed as an image by the display means 4 via the image-forming means 113, which can let the operator 120 know the positional relations of his fingers and the virtual object. Thus, it is realized that the operator 120 operates the virtual object by his fingers.

Such a position detecting method by the optical fibers can provide a wide range of positional information of the fingers, since it does not restrict the movement of the fingers and the arm of the operator 120. Furthermore, the positions and postures of the palm can be detected by a position/posture sensor mounted to the glove 110. As a position/posture sensor, a device which uses magnetism or an ultrasonic wave may be used. Furthermore, in the case of a remote manipulation, it can be applied by operating not the virtual object, but the actual object through the display means 4.

In such a conventional device, however, when operating the virtual object by detecting the positional information of the fingers, the operator has to confirm the positional relations of his fingers to the virtual object through the display means 4, and he cannot use the force sensation which is generally used when the human being operates objects. Therefore, it has been difficult for the operator to feel as if the virtual object exists and he is operating it.

On the other hand, as a means for exhibiting the force sensation, there has been proposed a method which provides a master manipulator having a shape corresponding to the fingers of the operator to control the manipulator by force (such as "artificial reality corresponding to the force sensation—development of a multi-dimensional force sensation feedback device" by Iwata, et al, at the 5th Human Interface Symposium, 1989). Sato, et al has proposed a method to give the force sensation by the tension of a thread, by stringing threads in space and operating the intersection points of the threads ("Interface device—SPIDAR—for the virtual working space" by Sato, et al, Shingaku Giho, PRU-88, 1989). However, either of them has a problem in that the device becomes big.

Furthermore, it is possible to add a force sensation feedback mechanism on the data glove of VPL Co., or to realize a force sensation feedback by mounting and controlling a motor with a position detector to the fingers. But it is usable only when the glove or the mechanism portion is attached. Therefore, it has a problem that when using it, it requires time to attach and detach the glove or the mechanism portion.

SUMMARY OF THE INVENTION

Considering these foregoing problems of conventional various devices, the present invention provides easily operable three-dimensional data input equipment which gives a repulsive force to the whole hand and also gives a bending angle of the hand and fingers and force sensation by a force sensation exhibiting device for fingers, or provides equipment which can move the position of the whole hand in a wide range of three-dimensional space.

The first aspect of the present invention is a housing which can be grasped by hand, wherein at least one of a rotatable motor or a linearly movable motor is contained.

The second aspect of the present invention drives intermittently a motor corresponding to a force vector to be given so that the torque is proportional to the magnitude of the vector, and in the intermittent drive, the period of turning off the motor is longer than the period until the activated motor stops.

The third aspect of the present invention provides a control means which repeats the activating motion, moving in the reverse direction, and stopping motion, in which a motor corresponding to the vector is activated so that the torque is proportional to the magnitude of the vector, and after being moved a certain distance or a certain angle, activated in an extremely low torque in the direction reverse to that of the former activation, and when it returns to the position or the angle before the activation is initiated, the motor is stopped.

The 4th aspect of the present invention provides a pressure detecting means on the surface of the housing with which the fingers contact to detect the pressure from the fingers.

The 5th aspect of the present invention comprises a data input device according to the fourth aspect of the present invention, an information processing means for processing the input data, and an image display means, wherein the image display means is equipped with a means for displaying the positions, postures and bending states of at least two fingers as the information corresponding to the data input device.

The 6th aspect of the present invention provides a pressure detecting means and a repulsive force generating means for generating a pressure in the direction reverse to the detected pressure on the surface of the housing with which the fingers contact.

The 7th aspect of the present invention provides a means for controlling a repulsive force generating means so that the pressure of the pressure detecting means becomes equal to the objective repulsive force.

The 8th aspect of the present invention comprises a force sensation exhibiting device, an image display means and a calculation means for calculating the force sensation value for exhibition, wherein the image display means is equipped with a means for displaying the positions, postures and bending states of at least two fingers as the information corresponding to the force sensation exhibiting means.

The 9th aspect of the present invention provides an auxiliary input means composed of a means for detecting a force of plural axes.

The 10th aspect of the present invention provides a section of an auxiliary input means and force sensation exhibiting device or a data input device on the same housing to operate the two input means by the right and left hands.

The 11th aspect of the present invention provides a force sensation exhibiting device for hands or a data input device for hands on one end of an arm portion and a polyaxes force sensor on the other end of the arm portion, to make an input to the polyaxes force sensor section by the overall operation of the force sensation exhibiting device section for hands or the data input device section for hands.

The 12th aspect of the present invention makes the shape of the device section grasped by the hand substantially cylindrical.

The 13th aspect of the present invention is mounted with a device for hands at the tip of a manipulator having multi degrees of freedom to give a repulsive force to the tip by a means for controlling the manipulator as well as by using a force applied to the manipulator as an auxiliary input.

The 14th aspect of the present invention provides a barrel shaped leaf spring in which the portion pushed by fingers corresponds to the central portion of the arc to control the radius of the leaf spring.

The 15th aspect of the present invention comprises a means for oscillatingly changing the radius of the barrel shaped leaf spring, the oscillating wave form being a wave form which repeats changing abruptly in the direction of increasing the radius, and changes moderately in the reverse direction, or the reverse action.

The 16th aspect of the present invention provides a switch operable by fingers not participating in the grasp, which makes it possible to stop temporarily the input of the change in the bending of the fingers.

The 17th aspect of the present invention provides a switch operable by fingers not participating in the grasp, which makes it possible to stop temporarily the input of the information of overall positions or postures of the fingers.

The 18th aspect of the present invention provides a switch operable by the non-grasping hand or an auxiliary input means, which makes it possible to stop temporarily the input of the change in the bending of the fingers or the information of overall positions or postures of the fingers.

The 19th aspect of the present invention controls bending of fingers in a remote area or virtual fingers based on the integral value or incomplete integral value of the detected force.

The 20th aspect of the present invention controls bending of fingers in a remote area or virtual fingers based on a value substantially holding the maximum value of the detected force.

The 21st aspect of the present invention comprises detecting means for detecting a displacement or a pressure at each section with which belly portions of a finger between each joint of the fingers contacts at the time of grasping to input data, such as the bending of each joint of the fingers.

The 22nd aspect of the present invention provides a means for adjusting the size of a diameter of substantially cylindrical shape.

The 23rd aspect of the present invention comprises a means for detecting a movement or a force of each finger in the left or the right direction, which makes the detected value as being the difference between the detecting values of two detecting means provided for each direction of the two directions.

The 24th aspect of the present invention provides a low-pass filter against the detected displacement or pressure and uses a value passed through the filter.

The 25th aspect of the present invention provides a means for calculating a dead zone which determines that there is no input when the detected displacement or pressure is below a certain value, and uses a value passed through the signal processing means.

The 26th aspect of the present invention subtracts the resulting value of the detecting means for detecting a displacement or a pressure which is the minimum but not zero, or the sum of the resulting values of all detecting means which detect displacements or pressures below a certain value, or the sum of the resulting value of the detecting means which detect displacements or pressures below a certain value obtained from the maximum displacement or pressure, from the respective detected resulting values of the displacement or pressure which is given from the contacts with the belly portions of the fingers between each joint of the fingers at the time of grasping, and makes the value the input data.

The 27th aspect of the present invention identifies in advance the interrelationship between the detected resulting value of the displacement or pressure which is given from the contacts with the belly portions of the fingers between each joint of the fingers at the time of grasping and the intention to bend the fingers of the person who grasps it, by using a neural network in which the detecting result is to be an input and the intention is to be an output, inputs the detected results to the identified neural network, and takes out the bending information of the fingers as an output to use it as an input.

The 28th aspect of the present invention provides an ultrasonic vibration motor comprising piezoelectric ceramics and an elastic body which generates a force in the same face with the belly portion of the fingers in the portion with which the belly portion between each joint of the fingers contacts at the time of grasping, and provides a means for detecting a displacement or a pressure in the vertical direction against the face of the belly portion of the fingers at the lower part of the ultrasonic vibration motor.

The 29th aspect of the present invention comprises a reciprocal converting means for detecting a displacement or a pressure in the vertical direction against the face of the belly portion of the fingers to determine the reciprocal, and a means for determining a product of the objective value of the force to be given within the face of the belly portion of the fingers and the reciprocal converting means, and drives the ultrasonic vibration motor in proportion to the product.

The 30th aspect of the present invention provides an ultrasonic vibration motor comprising piezoelectric ceramics and an elastic body which generates a force in the same face with the belly portion of the fingers, in the portion with which the belly portion between each joint of the fingers contacts at the time of grasping, and makes an average current of the ultrasonic vibration motor to be the magnitude of the force within the contact face of the belly portion of the fingers.

According to the first and second aspects of the present invention, a repulsive force can be given to the grasping hand when the motor in the housing is activated. While the motor is off in the intermittent drive, a reverse and weak repulsive force is generated, but it is not sensed by the human hand. And when the motor is activated again, the repulsive force can be obtained, and the repulsive force in the rotating direction is held to be given to the whole hand.

Furthermore, according to the third aspect of the present invention, by reversing the motor during the period corresponding to the OFF period according to the second aspect of the present invention, it becomes possible for the movable portion to return to the center of the movable range even in the motor of a linear motion type, whereby the repulsive force of the linear motion is held to be given to the whole hand, without the movable portion coming to the dead end over the movable range.

According to the 4th aspect of the present invention, by detecting the strength of the pressure of the palm side of the fingers, the bending degree of the fingers for grasping a virtual object can be determined according to the strength by utilizing a force close to the intention of the operator.

According to the 5th aspect of the present invention, by using the input device of the fourth aspect of the present invention, the intention to bend the fingers given to the input device is displayed on the display means as a bending of the actual fingers, thereby it becomes possible to grasp or pick up the object within the display screen by utilizing the strength of the force to bend the fingers.

According to the 6th aspect of the present invention, it becomes possible to sense the repulsive force from the virtual object in the fingers by the repulsive force generating means.

According to the 7th aspect of the present invention, by detecting the pressure of the palm side of the fingers and controlling the repulsive force generating means so as to become a pressure to be exhibited, a repulsive force when grasping a virtual object by bending the fingers can be obtained freely.

According to the 8th aspect of the present invention, while the positions and angles of the fingers are displayed on the display means, the repulsive force is fed back to the fingers, thereby a complex work such as deforming the virtual object becomes possible.

According to the 9th aspect of the present invention, by using a force input in the auxiliary input means, the position and the posture of the hand in the calculator can be changed in a wide range without accompanying a large shift of a force sensation exhibiting device grasped by hand.

According to the 10th aspect of the present invention, by providing an auxiliary input means and a force sensation exhibiting device section for hands or a data input device portion for hands on a common housing and operating them by both hands, the operator can use his one hand to hold the input device housing alternately.

According to the 11th aspect of the present invention, a force input can be given to the polyaxes force sensor portion by operating the force sensation exhibiting device portion for hands or the data input device portion for hands by the whole one hand, thereby a wide range of positional data input by one hand and a minute positional data input by the palm can be made possible.

According to the 12th aspect of the present invention, by making the shape of the portion to be grasped cylindrical, the contact area at the palm portion other than fingers can be enlarged and the operator can support the device by the palm to make it easy to input the force information of each finger.

According to the 13th aspect of the present invention, a repulsive force can be generated to the whole wrist by the means for controlling the manipulator.

According to the 14th aspect of the present invention, by enlarging the radius of the barrel shaped leaf spring, the rigidity of the leaf spring in the direction pushed by the fingers decreases, and by making the radius small, the rigidity can be increased.

According to the 15th aspect of the present invention, by changing the rigidity oscillatingly, when the rigidity increases, the fingers feel as if they are pushed back, and when the rigidity decreases, fingers feel as if they are pulled in. But due to the nonlinearity of the human sense, only part of the rapid change can be sensed, therefore the sensation to be pushed back or the sensation to be pulled in can be generated continuously.

According to the 16th, 17th and 18th aspects of the present invention, by a switch operated by a finger not participating in the grasp, or a switch operated by a hand not participating in the grasp, the bending information of fingers or positions/ postures information of the fingers are fixed.

According to the 19th and 20th aspects of the present invention, since the force by the fingers is held by an integral means or a maximum value-holding means, the grasp of a virtual object or an object in a remote area can be continued, without exerting a big force continuously.

According to the 21st aspect of the present invention, the intention corresponding to the bending of each joint of the fingers can be detected by a detecting means corresponding to the bending of each joint.

According to the 22nd aspect of the present invention, by enlarging the size of a diameter of substantially cylindrical shape, it is possible to make the shape easy to grasp for people having large hands, and by making the diameter small, it is possible to make the shape easy to grasp for people with small hands.

According to the 23rd aspect of the present invention, by determining the difference of the detected results of the right and left sides, it can be possible to obtain the same detected results when fingers are small, and therefore a force or displacement cannot be detected from the two detecting means, and when fingers are large, a force or displacement can be detected simultaneously from the two detecting means.

According to the 24th aspect of the present invention, fine changes such as trembles of fingers and unevenness of the force can be removed by a low-pass filter.

According to the 25th aspect of the present invention, a faint force not related to the intention are removed by a means for calculating a dead zone.

According to the 26th aspect of the present invention, since the force not related to the intention, but related to holding of the device is relatively small, the influences of the force can be removed, and only the information relating to the intention to bend the fingers are taken out.

According to the 27th aspect of the present invention, since the force relations between the intention to bend the fingers and the force to hold the device is identified preliminarily as a neural network, the information of the intention to bend the fingers can be taken out as an output by inputting the detected results to the neural network.

According to the 28th and 29th aspects of the present invention, it becomes possible to generate a force in the direction of the inner surface of the fingers by an ultrasonic vibration motor, and even if the force to push vertically against the surface of a finger is changed, the change is detected, and when the pushing force is weak, the magnitude of the force can be changed to correct the weakness, thereby a force along the objective value can always be generated.

According to the 30th aspect of the present invention, since the electric current of the ultrasonic vibration motor corresponds to the magnitude of the load, the load can be detected by the current, and the force given by the fingers in the inner face direction of the belly of the finger can be detected.

BRIEF DESCRIPTION OF DRAWINGS

FIGS. 3(a)–3(d) are signal waveform diagrams of the force sensation exhibiting circuit in the rotating direction in one embodiment of the present invention.

FIG. 4 is a circuit block diagram exhibiting a force sensation in the linear direction in one embodiment of the present invention.

FIGS. 5(a)–5(d) are signal waveform diagrams of the force sensation exhibiting circuit in the linear direction in one embodiment of the present invention.

FIG. 6 is a structural perspective view of the data input device in one embodiment of the present invention.

FIG. 7 is a sectional view of the data input device in one embodiment of the present invention.

FIGS. 29(a) and (b) are views showing one embodiment of the diameter adjusting means of a cylindrical device in one embodiment of the present invention.

FIGS. 42 and 43 are views of operational shapes showing the operational principle of the ultrasonic vibration motor in one embodiment of the present invention.

FIG. 44 is an enlarged view of the operational shapes showing the operational principle of the ultrasonic vibration motor in one embodiment of the present invention. FIG. 45 is a structural sectional view and a signal processing circuit diagram in one embodiment of the present invention.

PREFERRED EMBODIMENTS

The embodiments of the present invention will now be described in detail with reference to the accompanying drawings.

Figure 1:
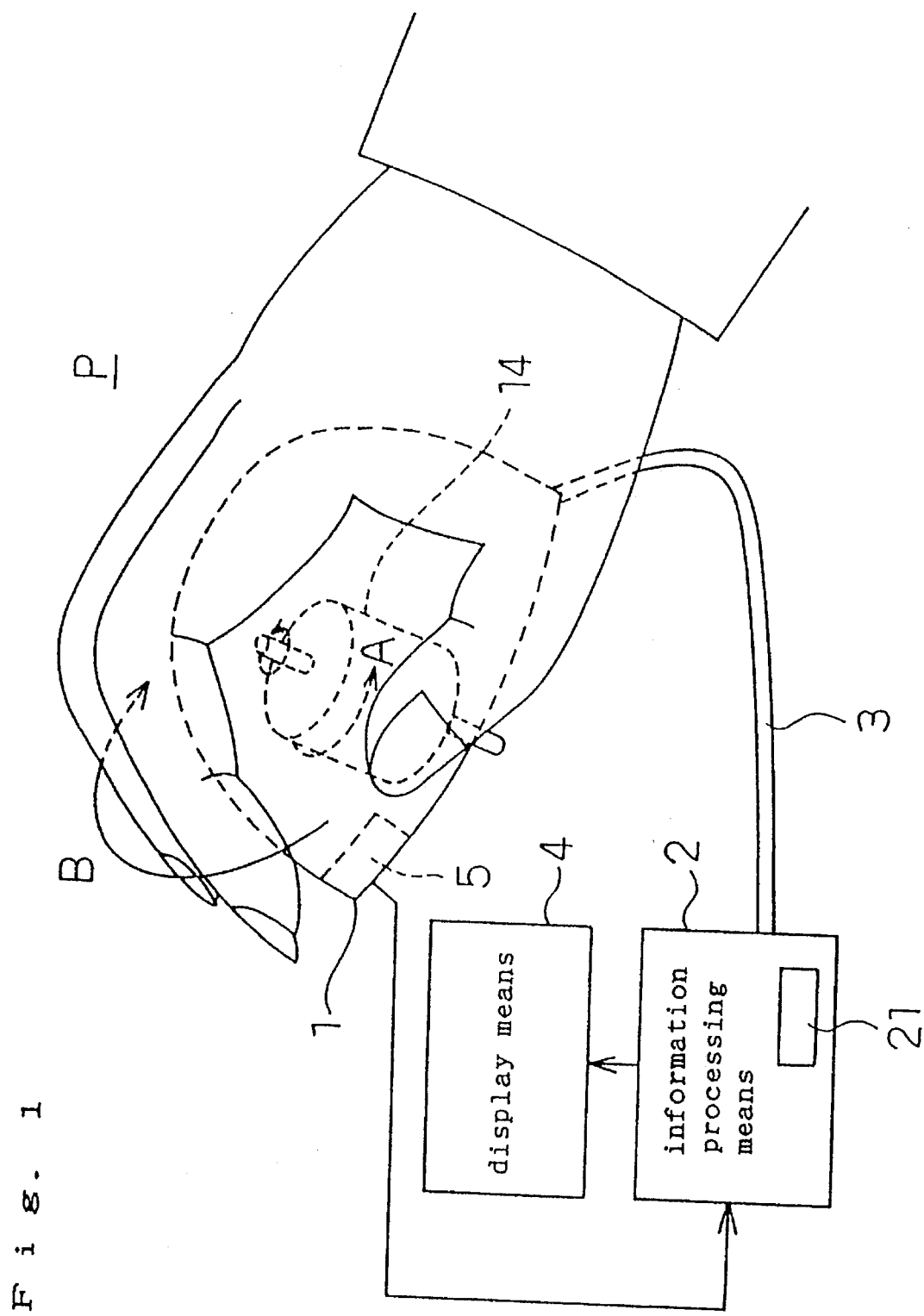
FIG. 1 is a perspective view showing the relation between the force sensation exhibiting device and the information processing means in one embodiment of the present invention.

FIG. 1 is a view showing the relations between the force sensation exhibiting device, the information processing means and the display means in one embodiment of the present invention. The force sensation exhibiting device 1 is connected to the information processing means 2 via a cable 3. The information relating to the exhibition of the force sensation are displayed on the display means as image information. The operator can easily know the cause why the force sensation is obtained, by seeing the display screen. Incidentally, the information processing means 2 can know at any time the information about the position of the force sensation exhibiting device 1 in three-dimensional space, as a position-detecting means 5 is mounted, for example, on the force sensation exhibiting device 1. In the memory 21 of the information processing means 2, adequate information of the repulsive force respectively corresponding to various positional information are housed in advance in the form of a table. For example, in the case that a hand comes to the place P where the hand hits against the wall, a repulsive force is caused, and in a place other than P, the repulsive force is to be 0. When the operator moves the force sensation exhibiting device 1, the position-detecting means 5 detects the position, the information thereof is input to the information processing means 2, and the table in the memory 21 is referred to in order to calculate if it is necessary to give a repulsive force or not by the information processing means 2, and the necessary information of a repulsive force is transmitted from the information processing means 2 to the force sensation exhibiting device 1. The force sensation exhibiting device 1 generates a repulsive force based on the repulsive force information by means of a built-in repulsive force generating means 14. The principle which becomes the basis of the generation of the repulsive force uses the acceleration by means of a motor 14 disposed in the inside of the force sensation exhibiting device 1. That is, by a rotation of the motor in the direction shown by an arrow A, a hand receives a repulsive force in the direction shown by an arrow B. The embodiments according to the first, second and third aspects of the present invention will now be described with reference to FIGS. 2, 3, 4 and 5.

Figure 2:
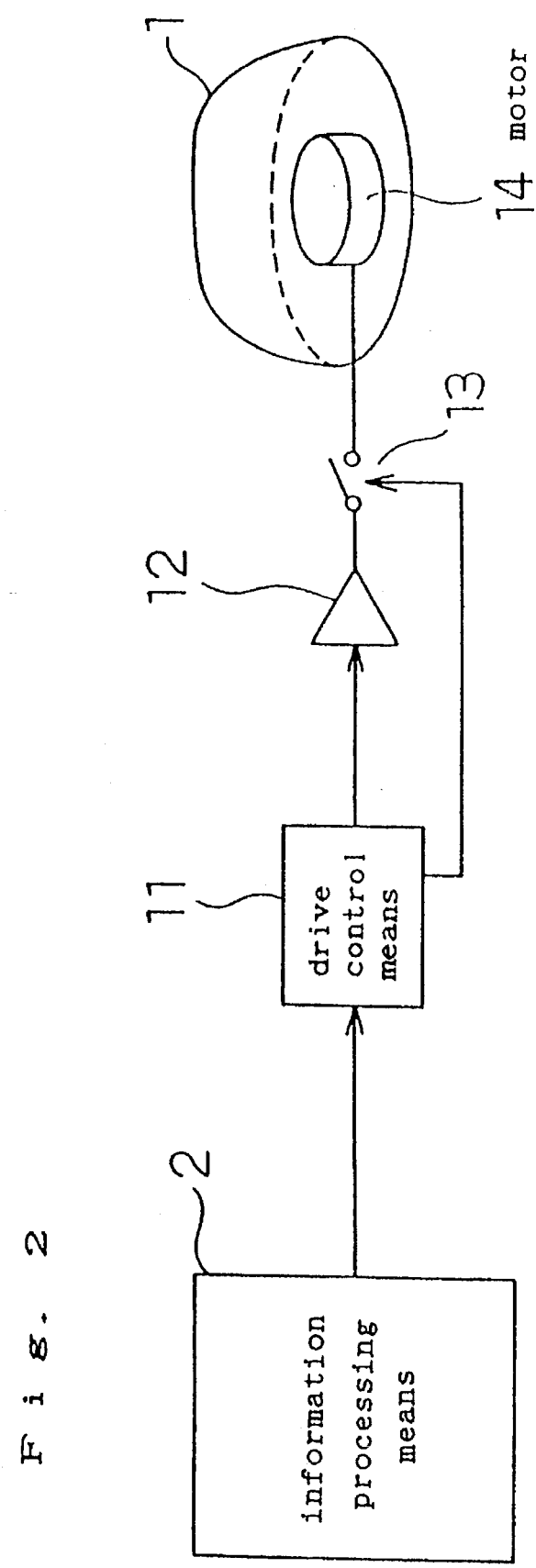
FIG. 2 is a circuit block diagram exhibiting a force sensation in the rotating direction in one embodiment of the present invention.

FIG. 2 is a block diagram illustrating the circuit for exhibiting the force sensation in the rotation direction, and FIGS. 3(a) to 3(d) are signal waveform diagrams showing the principle of the control operation. The necessary force sensation information determined at the information processing means 2 are input to the drive control means 11. The drive control means 11 inputs an instruction signal to a drive circuit 12 and a switch circuit 13 of the motor 14. Since the drive circuit 12 is connected to the motor 14 via a switch circuit 13, the ON/OFF operation of the motor becomes possible. Next, the method of drive control and the principles of operations are described with reference to FIGS. 3(a) to 3(d). The signal of FIG. 3(a) shows the necessary repulsive force information output from the information processing means 2. That is, it is assumed that the instruction of a "large" repulsive force is output from the time t1 to t2, and the instruction of a "no" repulsive force is output from the time t2 to t3, and the instruction of a "small" repulsive force is output from the time t3 to t4. The signal shown in FIG. 3(b) is an output signal waveform of the drive control means 11. The drive control means 11 drives the motor intermittently responsive to the instruction of a "large" repulsive force. The drive level during ON is a large drive level corresponding to the repulsive force. The time width during the ON pulse is set to be a time width in which the motor can be activated and the velocity is in an accelerated state. The time width during the OFF pulse is set to be longer than the time when the activated motor 14 stops. On the other hand, in the case of "no" repulsive force, the drive control means 11 keeps its drive instruction to the motor 14 OFF. Furthermore, in the case of a "small" repulsive force, the drive control means 11 drives intermittently by a not so large ON pulse. FIG. 3(c) shows the velocity response of the motor 14 responsive to the drive instruction of FIG. 3(b). When the ON pulse is applied, the motor 14 is activated, and the velocity increases rapidly. Since the ON pulse is made OFF while the velocity is unsaturated, the velocity of the motor 14 begins to decrease and stops soon. When the repulsive force is large, the increase of the velocity at the time of activation is fast, and when the repulsive force is small, the increase of the velocity at the time of activation is relatively slow. FIG. 3(d) shows the acceleration response of the motor 14. When the ON pulse is applied, a relatively large acceleration is obtained in the positive direction, and a relatively small acceleration is obtained during the OFF period until the motor is stopped. Furthermore, there is a difference in the magnitude of the acceleration depending on the magnitude of the ON pulse. On the other hand, when a certain object is held, if the object causes an acceleration in order to start a motion, the person who is holding the object gets a repulsive force which is equal to the product of the acceleration and the mass of the object. Therefore, when the acceleration shown in FIG. 3(d) is caused, the operator can feel a repulsive force in the direction reverse to that shown in FIG. 3(d). Furthermore, human sense has a nonlinearity and a detection limit which hardly senses a small stimulus, therefore the acceleration during the OFF period cannot be detected. Accordingly, the acceleration sensed during the ON period can be sensed as a repulsive force.

FIGS. 4 and 5(a) to 5(d) are signal waveform diagrams showing the circuit structure and the principles of the control operations in the case where the repulsive force is caused in the rotation direction with respect to the repulsive force in the linear direction. In the case of the shift in the linear direction, the shift range is limited, and a repulsive force cannot be generated continuously in the same control method as that of the rotation direction. Referring to FIG. 4, the repulsive force information output by the information processing means 2 is input to the profile converting means 21. The profile converting means 21 outputs a position control instruction corresponding to the repulsive force information. The position control instruction is input to the position control circuit comprising a comparator circuit 22, a drive circuit 23, a linear motor 26, a position detector 25, and a position detecting circuit 24, whereby the linear motor 26 is operated as the position control instructions. FIGS. 5(a) to 5(d) are signal waveform diagrams showing the control operation of the circuits shown in FIG. 4. The waveform of FIG. 5(b) shows a waveform of the position instruction signal by the profile converting means 21 with respect to the objective repulsive force shown in FIG. 5(a). The profile converting means 21 outputs an instruction to return gradually to the original position after shifting abruptly, when it is necessary to generate a repulsive force. The shift volume when shifting abruptly corresponds to the magnitude of the required repulsive force. The waveform in FIG. 5(c) shows a velocity of the linear motor 26 with respect to the position instruction. Similarly, the waveform in FIG. 5(d) shows the acceleration. In the waveform of FIG. 5(d), a relatively large acceleration is obtained intermittently, and a small acceleration is obtained except for the above case. The larger acceleration can be detected by the operator, and the smaller acceleration is below the limit which can be detected by the operator. Therefore, the operator can sense a repulsive force only in the direction which requires a repulsive force.

As described with reference to FIGS. 2, 3(a)–3(d), 4 and 5(a)–5(d), a repulsive force sensation can be given in the rotation direction and in the linear direction with respect to the force sensation exhibiting device 1. Incidentally, though not described in the above drawings, three directions are required in the rotation direction, and three directions are required in the linear direction in order to express all the actual repulsive forces. It can be realized by mounting motors corresponding to these directions in one device.

A section to input the bending of each finger, which is one embodiment of the data input device according to the 4th aspect of the present invention, will now be described. FIG. 6 is a perspective view thereof. A data input device 30 which can be commonly used with the force sensation exhibiting device of FIG. 1 is connected via a cable 3 to the information processing means 2, which is connected to the display means 4. The operator holds the data input device 30 by covering it with his/her hand. At that time, the tip portions of the first finger and the second finger are put on the depressions 33 and 34 on the surface of the data input device 30. The depressions 33 and 34 have pressure sensors 31a, 31b, 31c, 31d, 31e, 32a, 32b, 32c, 32d, and 32e mounted thereon to detect the force pushed by a finger. For example, when it is held by the right hand, in the case of the first finger, the belly portion of the finger is put on the depression 34, and the force to bend the whole first finger is detected by a pressure sensor 32d. Furthermore, the force to extend the first finger ahead is detected by a pressure sensor 32a, the force to bend the first finger forward is detected by a pressure sensor 32e, the force to shift the first finger to the right is detected by a pressure sensor 32b, and the force to shift the first finger to the left is detected by a pressure sensor 32c. As the pressure sensor, there can be used a pressure sensitive-type conductive rubber. Thus detected force of the finger is transmitted to the information processing means 2 which has stored the preliminarily housed relations between the pressure and the bending degrees of the fingers, and by confirming on the display by means of a display means 4, it is used as the equivalent information to the position information of plural points by, for example, plural pointing devices. Furthermore, the information relating to the force of the fingers can be used as the bending degrees of the fingers or of what is equivalent to the fingers in order to operate an object in a remote area or a virtual object.

FIG. 7 is a sectional view of the data input device 30 described in FIG. 6 cut in the straight direction with the finger put thereon, that is, cut at right angles to the longer side direction of the depression. The depression 34 is shown in blank. Furthermore, the pressure sensor is drawn in the order of 32c, 32d and 32b from the right. And the pressure sensor is covered with a cover 36 so that the pressure sensor does not touch directly to the belly portion of the finger. The pressure change by the finger is transmitted through the amplifying circuits 35c, 35d and 35b to the information processing means 2.

Figure 8:
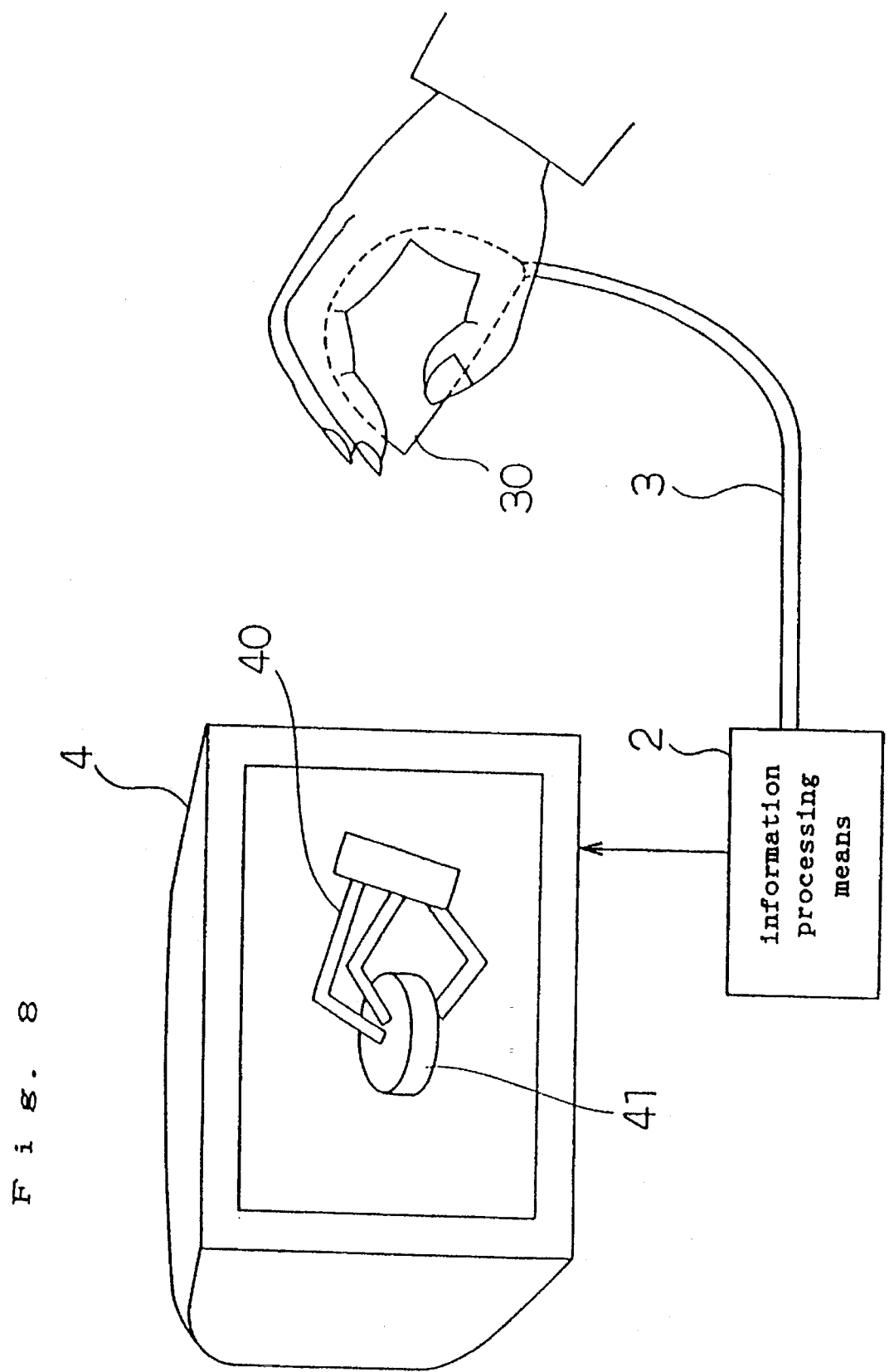
FIG. 8 is a perspective view showing the using condition of the data input device in one embodiment of the present invention.

FIG. 8 is a perspective view showing one embodiment of the data input device according to the 5th aspect of the present invention. The data input device 30 described in FIG. 6 and FIG. 7 is operated by being held by hand. The intention to bend the fingers based on the pressure of the belly portion of the fingers input to the data input device 30 is transmitted through a cable 3 to the information processing means 2 and converted to the bending angles of virtual fingers. The bending angles of virtual fingers are displayed directly by the shape of the fingers as shown by a virtual object 40 in the screen by the display means 4. The first finger and the second finger are drawn from the upper side and the thumb is drawn from the bottom side. At that time, the positional interrelations with the virtual object 41 is also displayed as an image. Since the operator carries out the operation of the data input device while seeing this display, he/she can easily operate the virtual object 41. Incidentally, the data input device used in FIG. 8 requires a detector for detecting the position and posture of the hand in space, but the shape and the method to be attached are known conventionally, therefore the concrete description thereof is omitted in FIG. 8.

Figure 9:
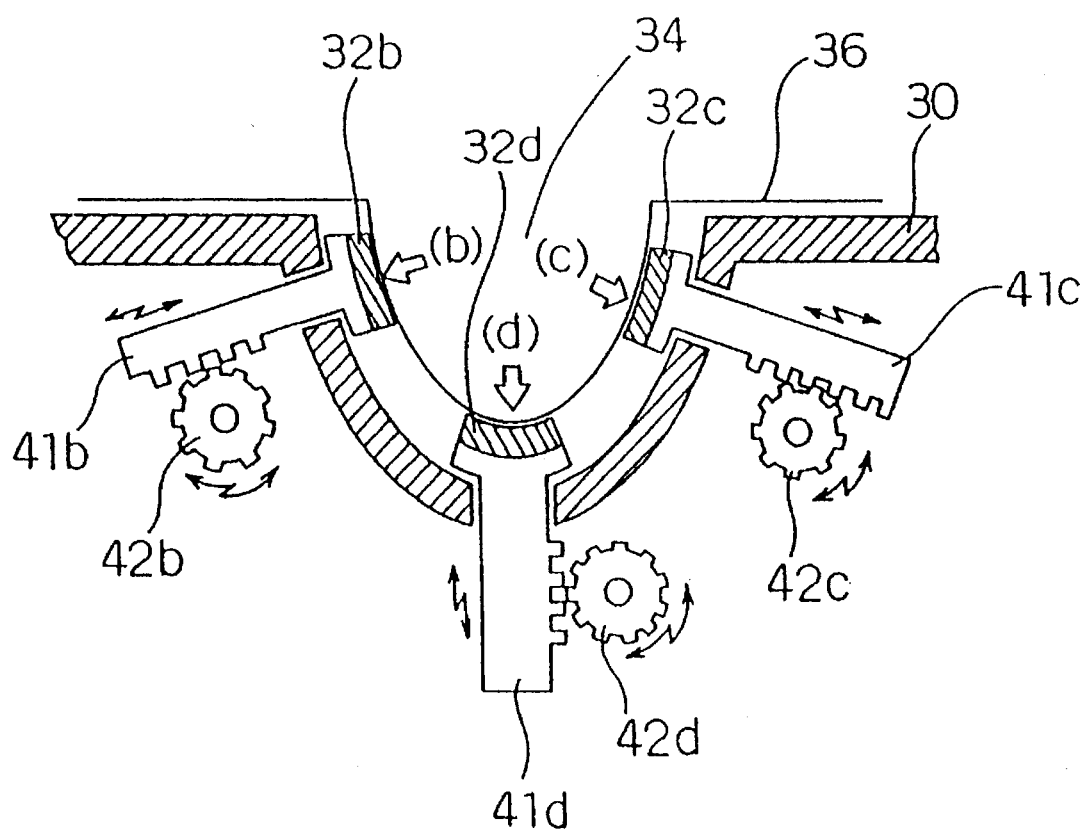
FIG. 9 is a structural sectional view of the repulsive force generating mechanism in one embodiment of the present invention.

FIG. 9 is a structural sectional view showing one embodiment of the part which gives a repulsive force to the fingers of the data input device 30 according to the 6th aspect of the present invention. Pressure detecting sensors 32c, 32d and 32b are provided as in FIG. 7 with respect to the depression 34 on which the belly portion of the finger is put. Respective pressure sensors are mounted on the movable portions 41c, 41d and 41b, and by rotating the driving axes 42c, 42d and 42b, the pressure sensors can be controlled to move in the direction of the contact with the finger by the relation of gears of pinions and racks by rotating the driving axes 42c, 42d and 42b. In FIG. 9, the driving method is shown by an example of the rotation system, but it is clear that it is possible to drive the movable portions 41c, 41d and 41b by using linear type motors such as a voice coil motor. Furthermore, a displacement detecting means may be used instead of the pressure sensor.

Figure 10:
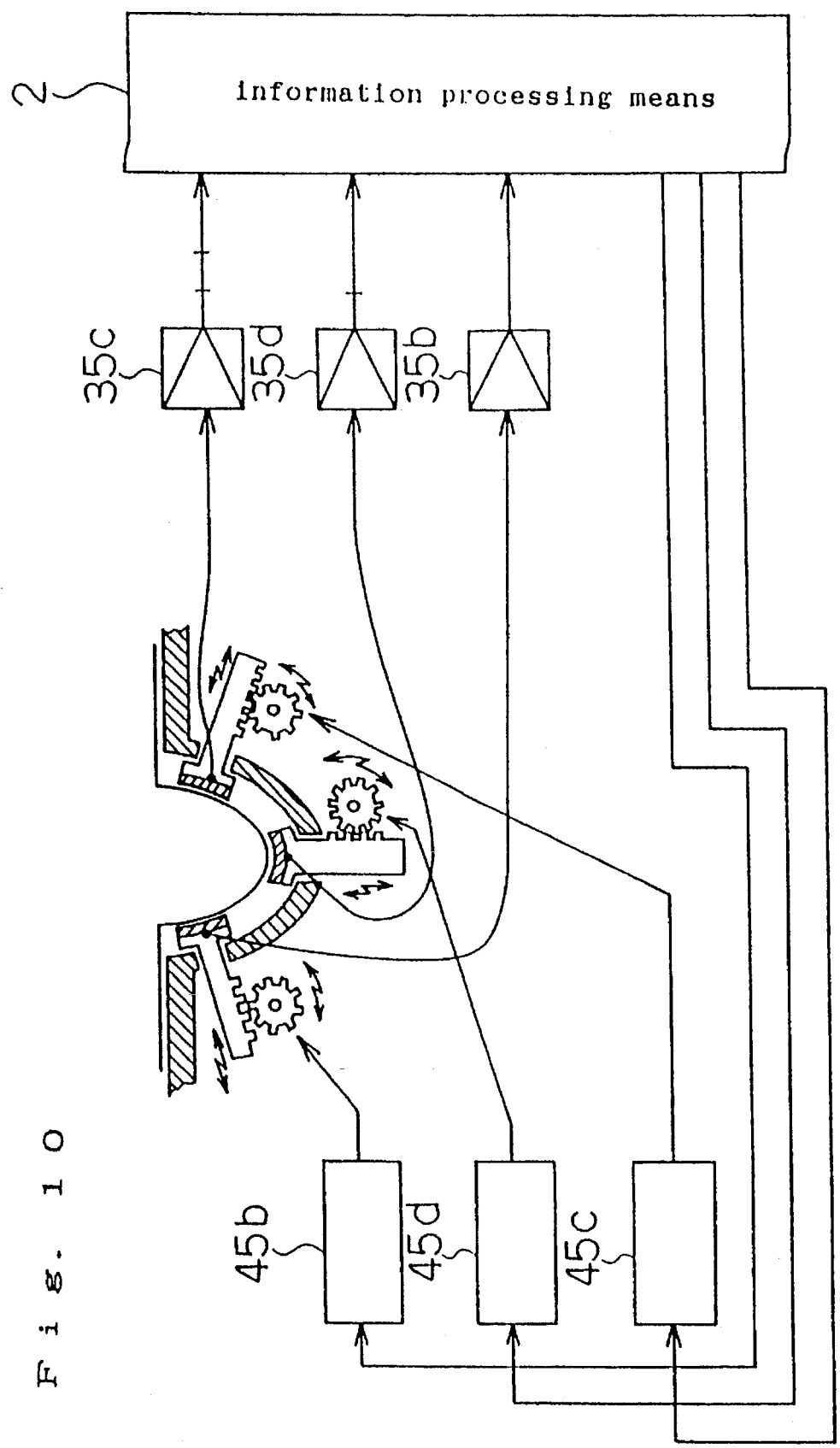
FIG. 10 is a circuit block diagram for controlling a repulsive force in one embodiment of the present invention.

FIG. 10 is a block diagram of a circuit illustrating the structure of the control system according to the 7th aspect of the present invention. The pressure information P detected by the pressure sensors are transmitted through the amplifiers 35c, 35d and 35b to the information processing means 2. The information processing means 2 transmits a force instruction F with respect to the detected pressure p to the drive control means 45c, 45d and 45b by means of the following calculation:

$F = kp$ wherein, k is a constant in the range of $-1 < k < 1$, and when k is close to 1, a large repulsive force can be obtained, and a feeling to push a hard thing is obtained. When k is close to −1, since it acts in the direction to accelerate the force of the finger, a feeling to push a soft thing is obtained. The information processing device 2 assumes that, for example, when the finger hits against the virtual object, k= 1, and when the finger does not hit against it, k= −1, and can freely express a hard feeling and a soft feeling by changing k. For example, it controls so that the detected pressure becomes equal to the value of the desired force sensation to be exhibited.

Incidentally, in the embodiments of FIG. 9 and FIG. 10, the pressure in all the directions with respect to the belly portion of the finger is detected, and the embodiments which can cause a repulsive force similarly in all the directions are taken up for the explanation. But it can easily be thought that it may be a device which can detect and control only the direction pushed by the finger. Furthermore, though the embodiment using a pressure sensor to detect the pressure is taken up for the explanation, the method to calculate the force pushed by the finger by utilizing the change of the motor with respect to the driving axes 42b, 42c and 42d and the drive load may be possible. Furthermore, in FIG. 6, there is described a case where only the belly portion at the tip of the finger can be detected and controlled, but it is obvious that the detection and control of the pressure of other portions of the finger can be possible in the same manner.

The structure to give a repulsive force to fingers and the control method thereof are described with reference to FIG. 9 and FIG. 10, but as a simple method, there may be used a method to let the finger acknowledge that the fingers contact a virtual object by using an oscillation instead of giving a repulsive force. In this case, it can be easily realized by oscillating the driving axes 42c, 42d and 42b by a motor in FIG. 9. The oscillation repeats to change, for example, abruptly in the direction of the repulsive force, and to change moderately in the reverse direction.

Furthermore, in the above mentioned embodiments, a direct-current motor is used as a motor, however, it does not necessarily have to be a motor driven by an electromagnetic force, and it may be, for example, a so-called ultrasonic motor which utilizes the oscillation of a piezoelectric element.

The 8th aspect of the present invention will be described with reference to FIG. 8 again. FIG. 8 is a view also showing one embodiment which uses a data input device according to the 8th aspect of the present invention. The data input device (here, it is a force sensation exhibiting device) 30 described in FIG. 9 and FIG. 10 is operated and held by hand. The intention to bend the fingers based on the pressure of the belly portion of the finger input to the force sensation exhibiting device 30 is transmitted via a cable 3 to the information processing means 2 to be converted to the bending angles of virtual fingers. The bending angles of virtual fingers are displayed just as the shape of fingers as shown in the virtual object 40 in the screen by the display means 4. At this time, the positional interrelation with the virtual object 41 is also displayed as an image. When the position of the fingers in the screen contacts with the virtual object 41, the information processing means 2 displays the screen, whereby it is easily known that the positions of the fingers in the screen contacts with the virtual object 41. At that time, the information processing means 2 sends the instruction to give a large repulsive force to the force sensation exhibiting device 30. Since the force sensation exhibiting device 30 gives a repulsive force to the fingers, the operator can easily know that the tips of his/her fingers contact with the virtual object 41 and as well as the image output from the display means 4, whereby an operation with higher quality can be realized. For example, when the virtual object 41 is not a rigid body, but an elastic plastic body, such as a clay, a delicate deforming operation becomes possible.

Figure 11:
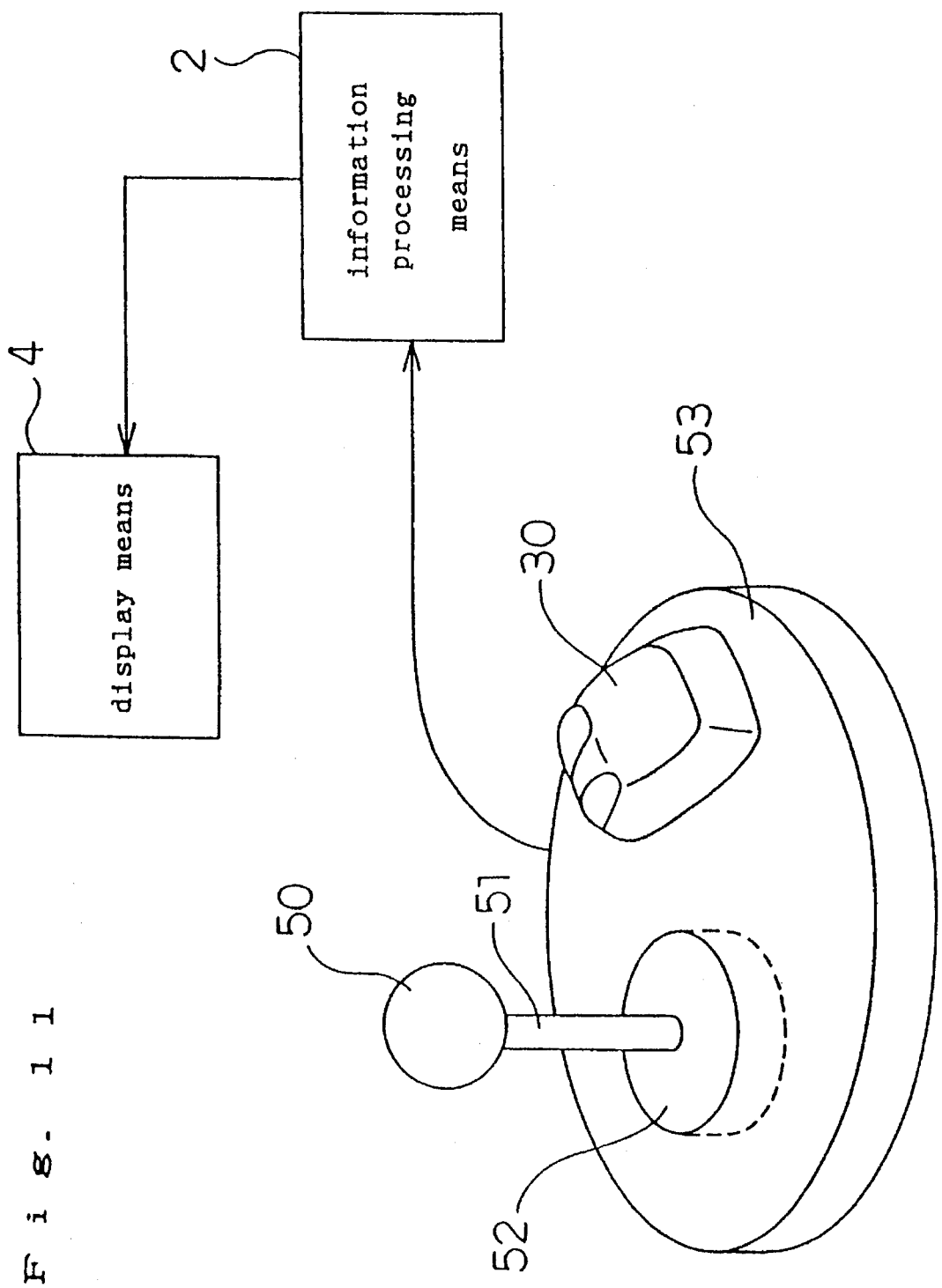
FIG. 11 is a perspective view showing the relations with the auxiliary input means in one embodiment of the present invention.

FIG. 11 is a perspective view showing the structure wherein an auxiliary input means is provided on a common housing according to the 9th and 10th aspects of the present invention. In FIG. 11, the delta input device 30 described with reference to FIG. 6 and the auxiliary input means 50, 51, and 52 are mounted on the common housing 53. The auxiliary input means is composed of a grip 50 which is grasped by the operator, a polyaxes force sensor 52, and a lever arm 51 which connects them. The operator puts his/her right hand on the data input device 30, and grasps the lever arm 51 and the grip 50 of the auxiliary input means by the left hand. When the operator tries to move the position of his/her hand in a virtual environment in the display means 4, he/she operates the lever arm 51 of the auxiliary input means to the corresponding direction. When he/she tries to operate the lever arm 51 in the longitudinal, lateral, oblique or rotational directions, the force in the corresponding directions can be detected by a polyaxes sensor 52. Since the direction of the force given by the operator coincides with the direction in which the finger in the display means 4 is moved, the information of the force can change the positions of the fingers in the display means 4 by the information processing means 2. Furthermore, by setting so that the positions of the fingers move a certain amount when a force is applied, it becomes possible that the fingers move in an infinitely large virtual space by making the time for applying the force longer. (The concrete principles and structures of the polyaxes sensor 52 are explained in "Force sensing-type sensor," Ogata, et al, Japanese Robotics Society, Vol. 6, No. 9, pp. 759–765, 1991). Thus, when the left hand operates the lever arm 51 for the auxiliary input, the right hand performs the role to support and fix the whole input device, and conversely, when the right hand intends to grasp an object and applies a force to the palm, the left hand performs a role to support and fix the whole input device. Therefore, the operator can easily operate the input device, even if the whole input device is small and light.

Figure 12:
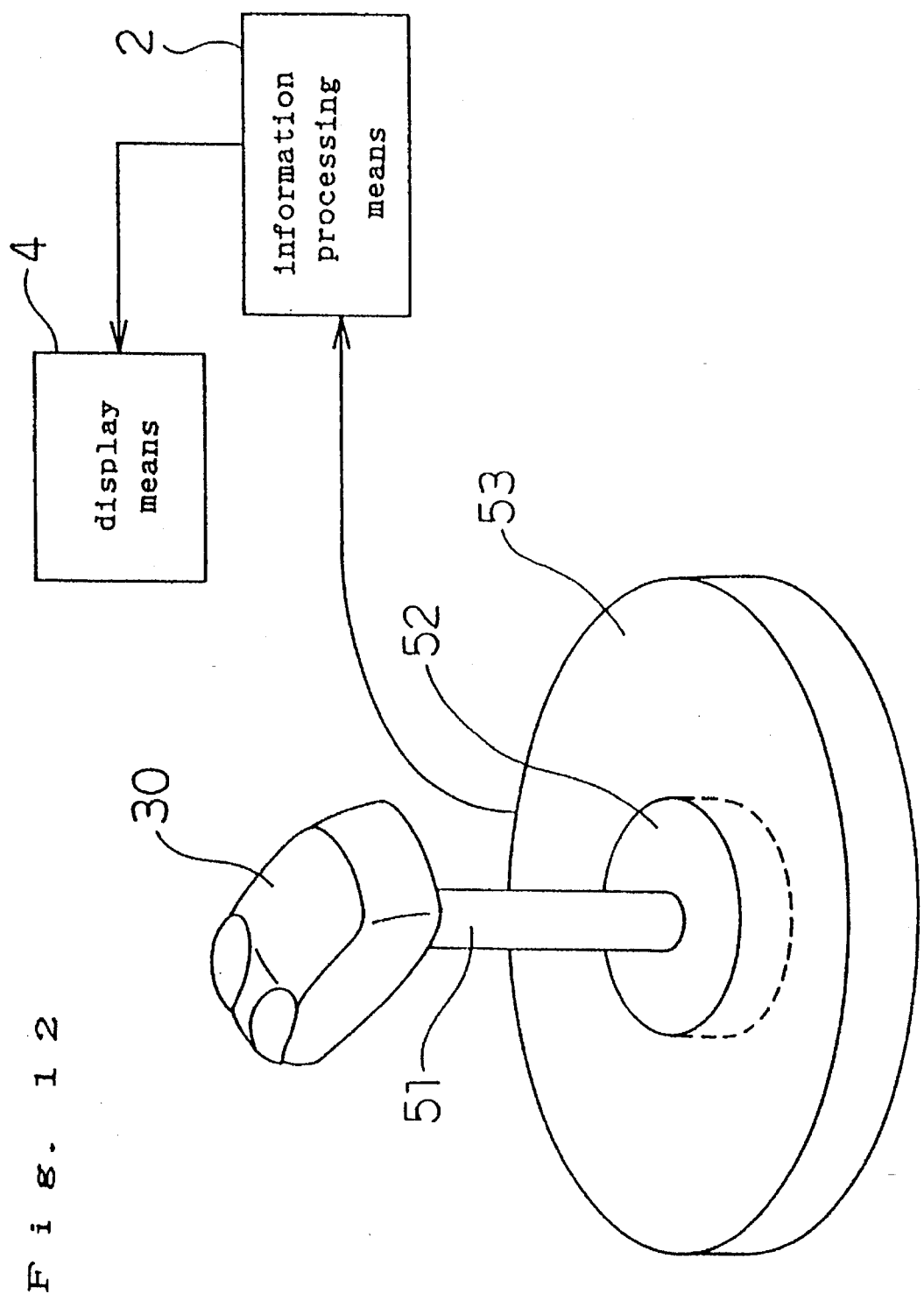
FIG. 12 is a perspective view showing the relations with other auxiliary means in one embodiment of the present invention.
Figure 13:
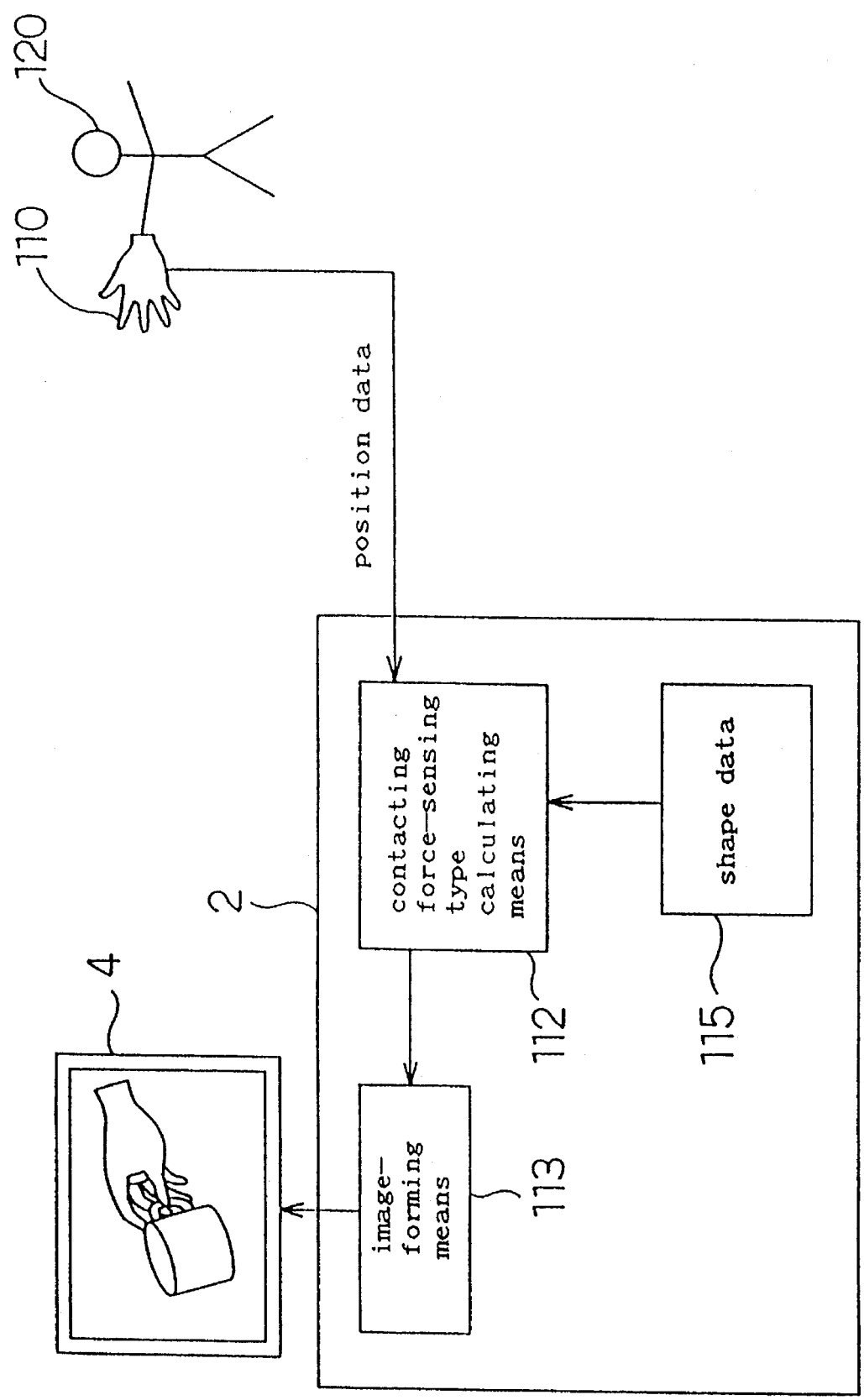
FIG. 13 is a block diagram showing a structural example of the conventional data input equipment.

FIG. 12 corresponds to the 11th aspect of the present invention, and is a perspective view showing another positional relationship between the auxiliary input means and the data input device portion different from that of FIG. 11. The auxiliary input means is composed of a lever arm 51 and a polyaxes force sensor 52, and a data input device portion (or a force sensation exhibiting device portion) 30 is fixed at the position of a grip 50 in FIG. 11. Thus, the operator can operate the auxiliary input simultaneously by only one hand. Concretely, by applying a force through the lever arm 51 toward the direction to which the operator intends to move it, while grasping the data input device portion (or a force sensation exhibiting device portion) 30 by the right hand, it becomes possible to move the fingers to the infinite distance in the display screen. Particularly in FIG. 12, since all the operations to apply a force can be performed by one hand, it becomes possible to support and fix the whole input device by the other hand, and the operator can easily operate the input device, even if the whole input device is small and light.

Incidentally, in FIG. 11, the embodiment in which the auxiliary input means is integrated with the data input device, the operation shown in FIG. 8 can be done by dismounting the data input device 30 and grasping it by hand to lift it.

Figure 14:
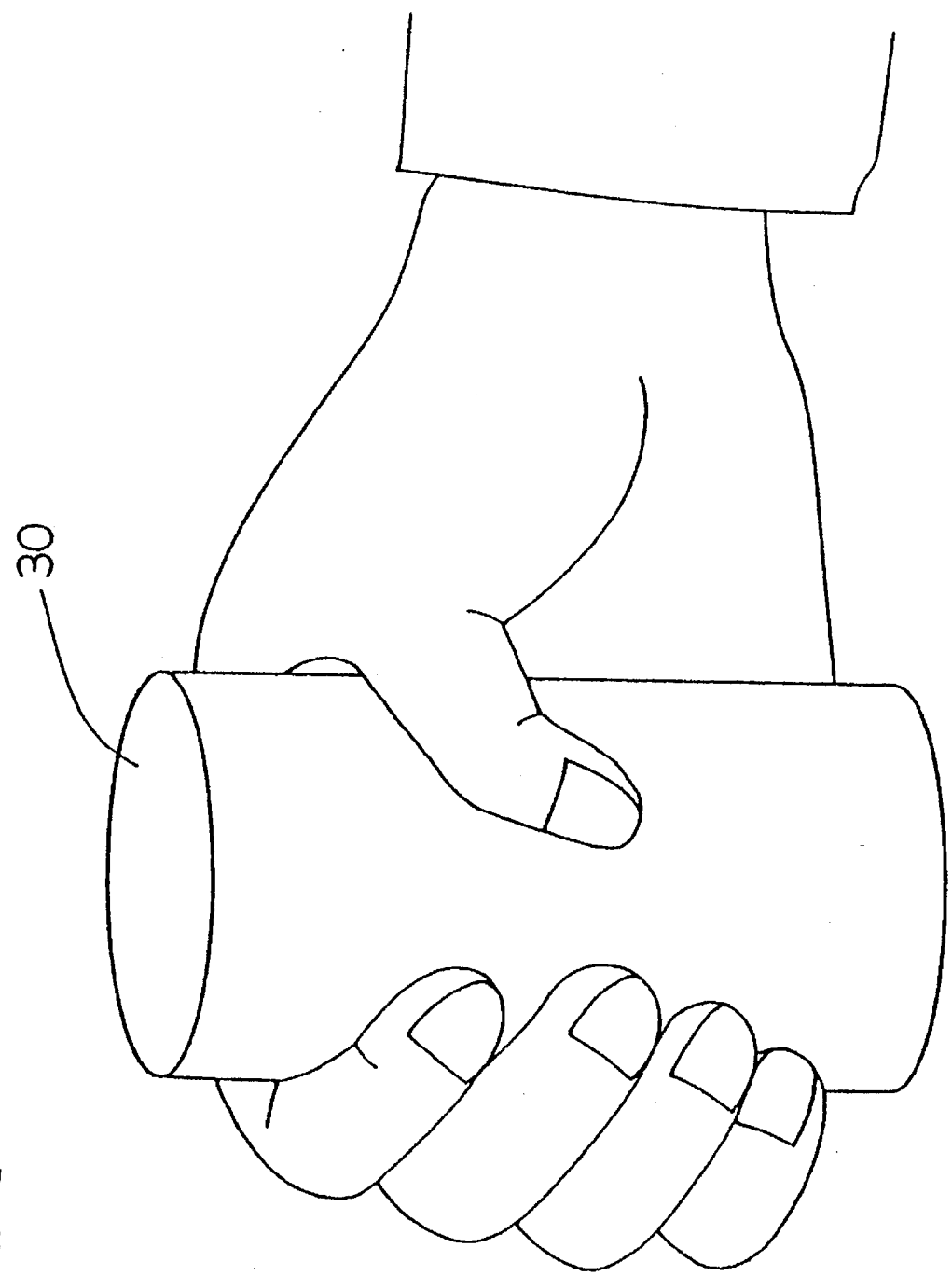
FIG. 14 is a perspective view showing the state holding a cylindrical device.
Figure 15:
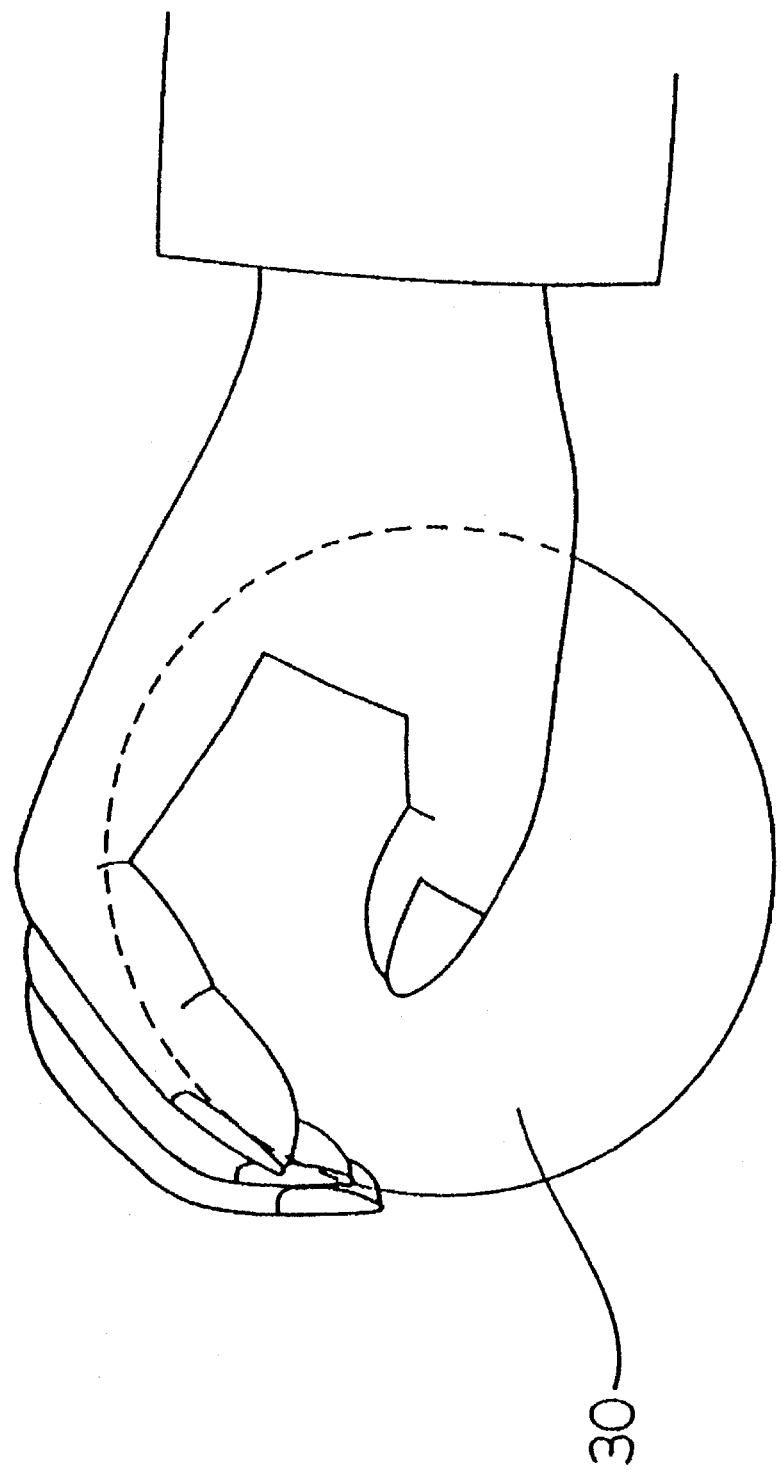
FIG. 15 is a perspective view showing the state holding a spherical device.
Figure 16:
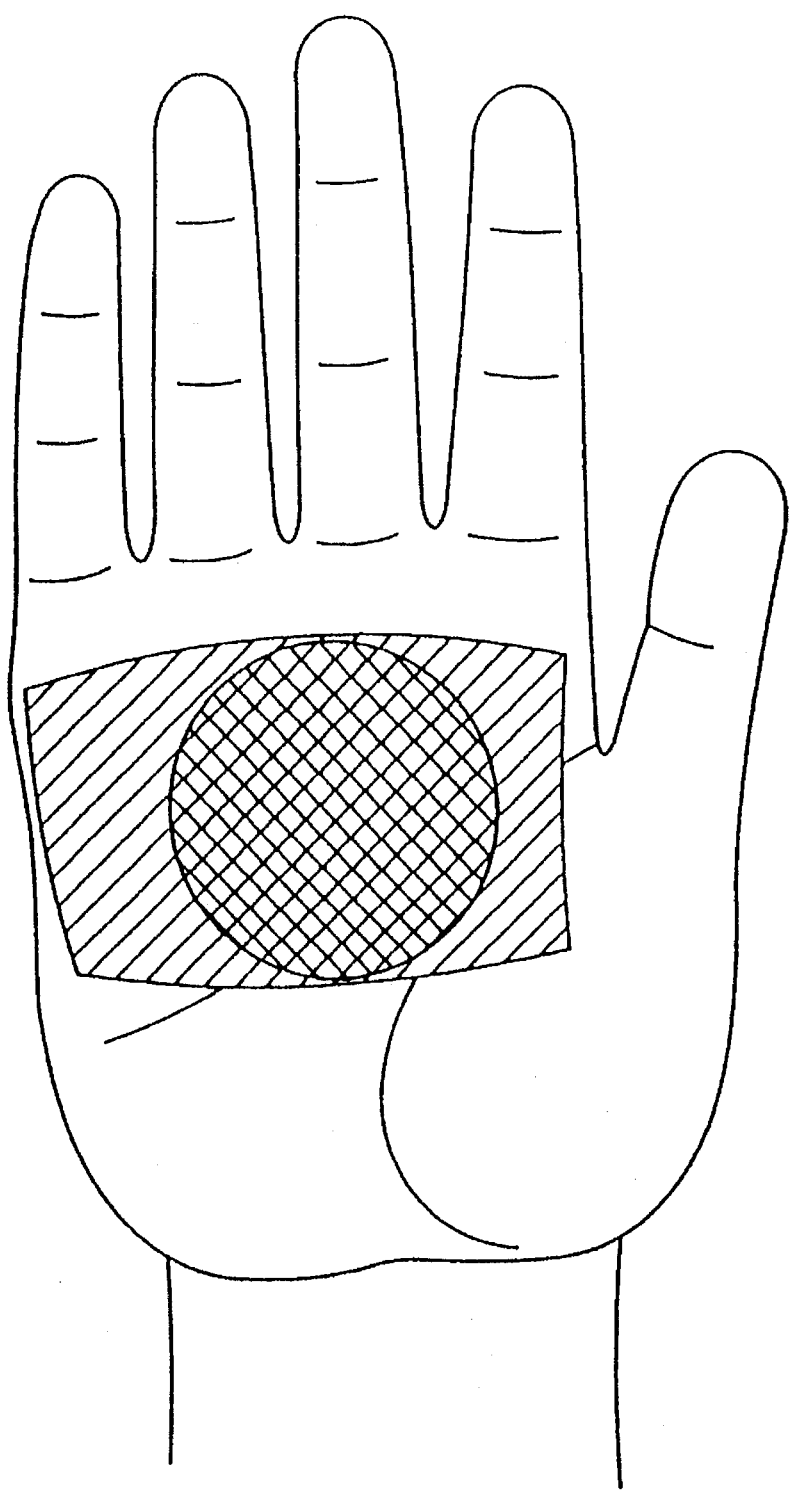
FIG. 16 is a perspective view showing a contact portion of the device with respect to a palm.

Next, the 12th aspect of the present invention will be described with reference to FIGS. 14, 15 and 16. FIG. 14 is a perspective view showing the holding state when the data input device or the force sensation exhibiting device 30 is cylindrical. FIG. 15 is a perspective view showing the holding state when the data input device or the force sensation exhibiting device 30 is spherical. FIG. 16 is a perspective view showing the contact face in the palm in the case of the two shapes illustrated in FIGS. 14 and 15. In the case of a cylindrical shape as shown in FIG. 14, the thumb and other fingers hold the device 30 so that the thumb opposes the other fingers. And in the case of a spherical shape, the device 30 is held so that the fingers cover the hemisphere face. In either case, the device 30 is held by hand. However, in the case of a cylindrical shape, since the thumb opposes the other fingers, the cylindrical face of the device 30 can be held so as to be covered by the palm portion. On the other hand, in the case of a spherical shape, since the oppositiveness of the thumb and other fingers is low, it is difficult to cover the device only by the palm to hold it, and the necessity to hold it by the fingers increases. Furthermore, even if the device 30 can be held by the palm, the contact area corresponding to the area held by the palm is the part shown by cross-line hatching in the case of a spherical shape, and it is narrower than the contact area of the cylindrical shape shown by hatching of an oblique line in FIG. 16. Moreover, from the viewpoint of friction, the cylindrical shape is advantageous. Incidentally, the explanation is done relating to a spherical shape here, however the hemispherical shape is held in the same manner as the spherical shape, whereby the content of the 12th aspect of the present invention is not affected. Furthermore, though depressions or pressure sensors for the fingers are omitted to facilitate the illustration, it is needless to say that they may be included as is obvious from the results of FIG. 6, and the like.

Figure 17:
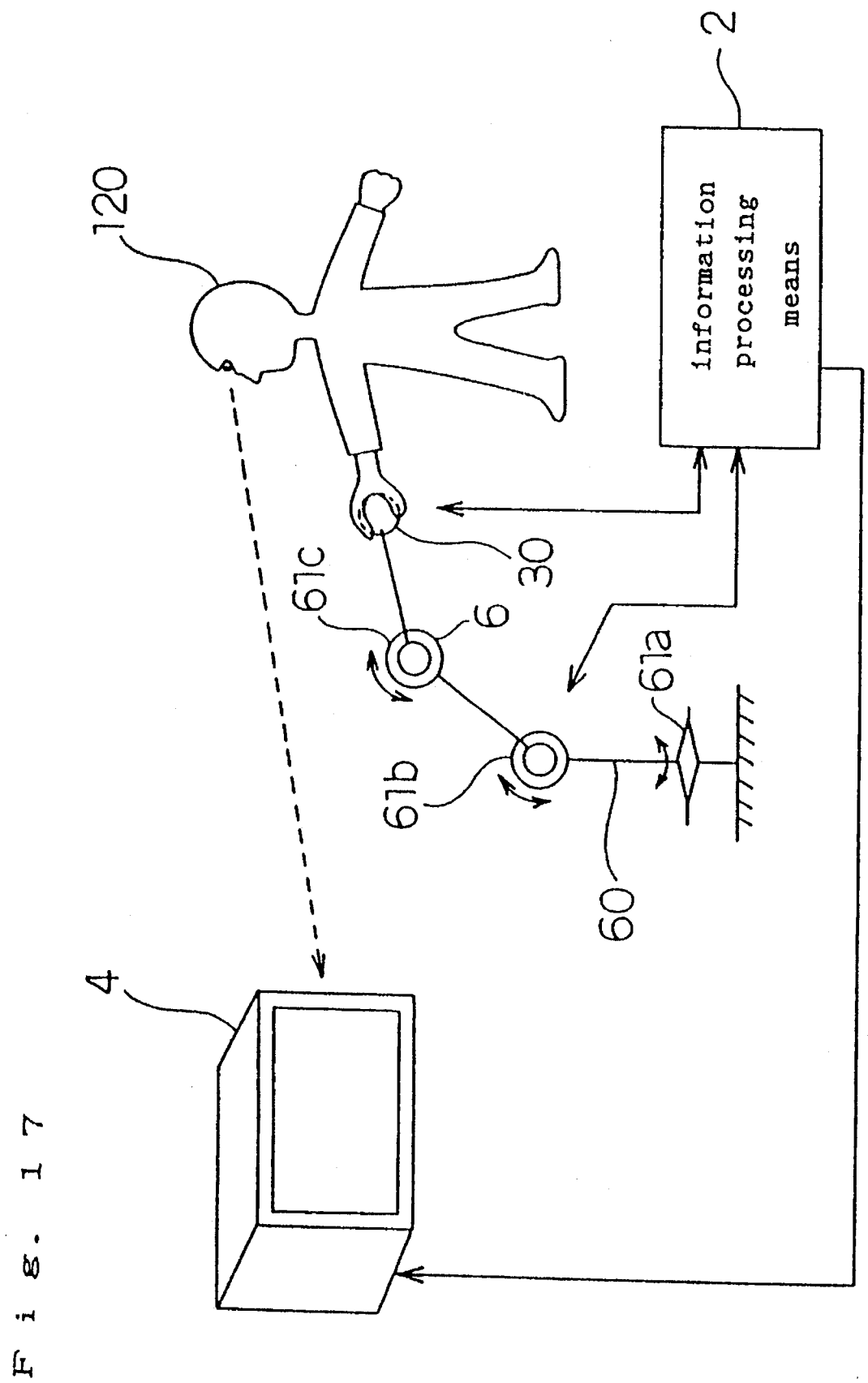
FIG. 17 is a perspective view showing the relation with a manipulator in one embodiment of the present invention.

Next, the 13th aspect of the present invention will be described with reference to FIG. 17. In FIG. 17, at the tip of a manipulator 60, a data input device or a force sensation exhibiting device 30 is mounted. The operator holds the device 30, and carries out the operation while seeing the display means 4. The shift of the position of the whole wrist is carried out while being restricted by the manipulator. The position of the whole wrist can be detected by the information processing means 2, by using the angle of each joint 61*a*, 61*b* and 61*c* of the manipulator 60. The calculated results are fed back to the operator 120 via the display means 4. Furthermore, the information processing means 2 controls the restriction of the manipulator 60. With regard to the control of restrictions, a force control, a compliance control and a position control is selected according to need. Thereby, it becomes possible to give a repulsive force to the operator 120 via a data input device 30 mounted at the tip of the manipulator 60. Incidentally, FIG. 17 is described by using a manipulator having three joints, but the present invention is not limited to the number of joints, and it is obvious that the present invention may be applied to a manipulator with one joint and a manipulator with an infinite joints.

Figure 18:
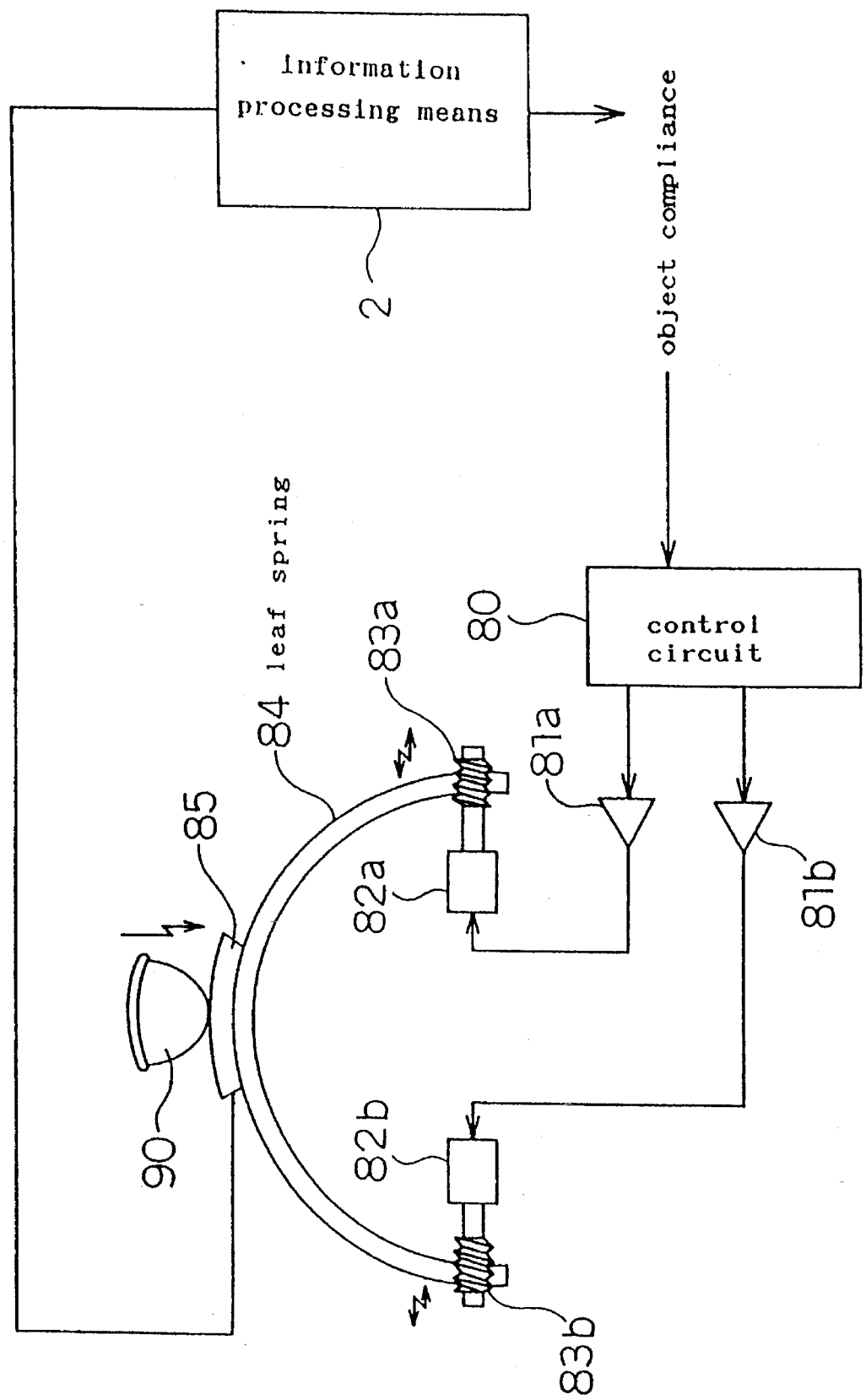
FIG. 18 is a structural sectional view of a compliance control means in one embodiment of the present invention.

FIG. 18 is a structural sectional view showing one embodiment according to the 14th aspect of the present invention. Fingers 90 push via a soft housing (not shown) to operate the pressure sensor 85 mounted on the barrel shaped leaf spring 84. The leaf spring 84 carries out a spring action by the push of the finger 90. The leaf spring 84 is fixed by gears 83*a* and 83*b* at both ends, and the length of the bowstring can be changed by the rotating action of the gears 83*a* and 83*b*. When the length of the bowstring is made longer by driving the gears 83*a* and 83*b* by motors 82*a* and 82*b*, the finger 90 can easily push downward and the spring becomes soft. On the contrary, when the length of the bowstring is made shorter, the finger 90 is pushed back upward, and the spring becomes hard. Thus, the softness (compliance) can be changed against the finger 90. The control circuit 80 calculates the necessary position with respect to the objective compliance to control the positions of motors 82*a* and 82*b*.

Figure 19:
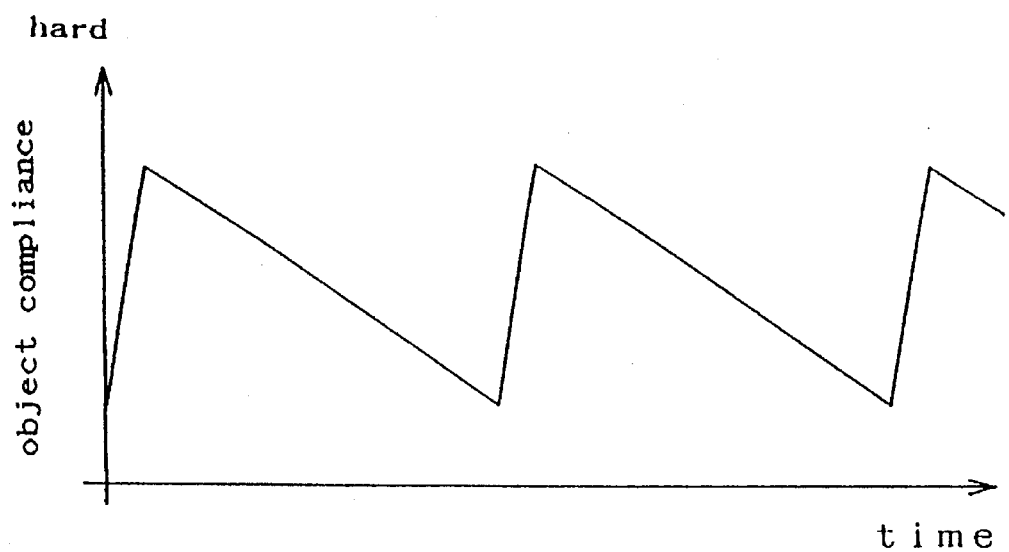
FIG. 19 is a waveform of a control signal of the repulsive force sensation in one embodiment of the present invention.
Figure 20:
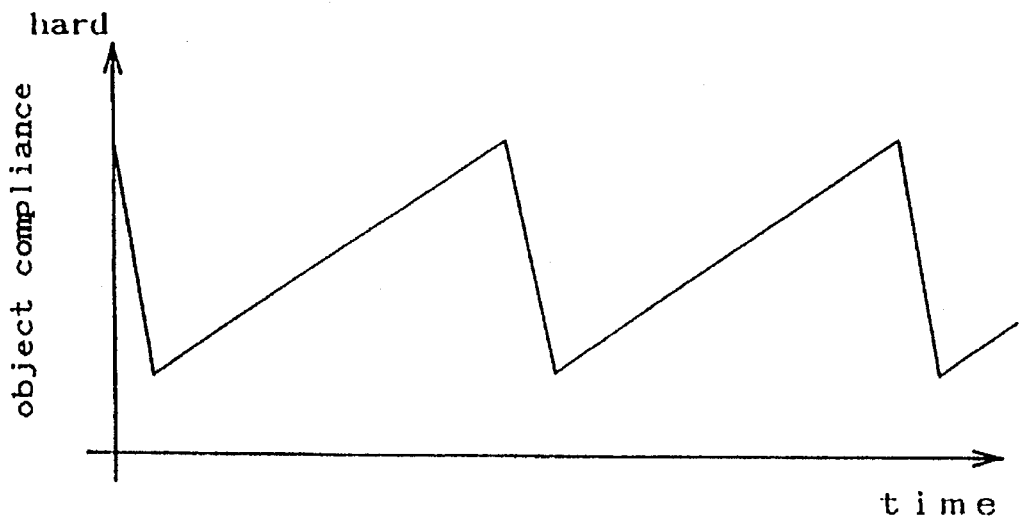
FIG. 20 is a waveform of a control signal of the repulsive force sensation in one embodiment of the present invention.

FIGS. 19 and 20 are the views showing the waveforms illustrating the action principles of the embodiment according to the 15th aspect of the present invention. The waveform of FIG. 19 shows the setting method of the objective compliance in order to give the sensation of a repulsive force in the direction of being pushed back, and the waveform of FIG. 20 shows the setting method of the objective compliance in order to give the sensation of a repulsive force in the direction of being pulled in. Since the action principles are the same, the explanation will be done by taking FIG. 19 as an example. The waveform of FIG. 19 is to repeat the actions to increase the objective compliance abruptly and to return it slowly to the original point. By doing this, since only the abrupt change can be sensed by a human body due to the nonlinearity of the human sense as described in the 1st aspect of the present invention, the operator feels it becomes harder. Since the actual finger is pushing the leaf spring 84 in FIG. 18 with a certain force, the finger is pushed back by the hardened portion, whereby the finger senses the repulsive force to be pushed back.

Figure 21:
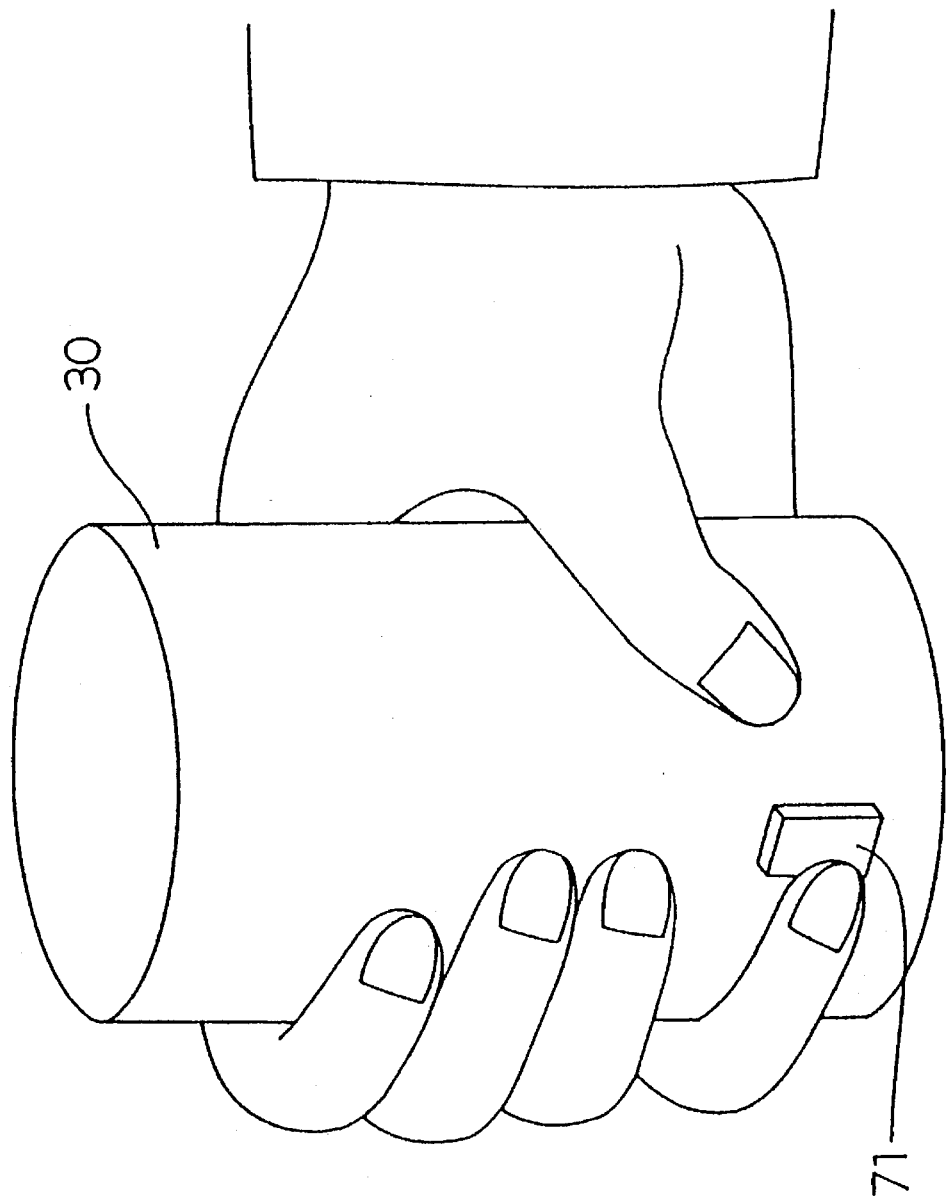
FIG. 21 is a perspective view showing the state of holding a device in one embodiment of the present invention.

FIG. 21 is a structural perspective view showing one embodiment of the 16th and the 17th aspects of the present invention. In the state of holding the device 30, a switch 71 operable by the little finger not participating in the hold is provided. According to the present invention described above, it is necessary to continuously give a certain force in the bending direction of the finger, thus other actions cannot be done on the way. The 16th aspect of the present invention makes it possible. Namely, by pushing the switch 71 during the operation, other actions can be performed in the state that the bending information of the fingers remains as it is. It can be easily realized to perform the decision and processing based on the input of the switch 71 by the information processing means 2 (not shown). Furthermore, once the switch 71 is turned ON, there is no need to continue pushing by the finger to prevent fatigue of the finger.

Figure 22:
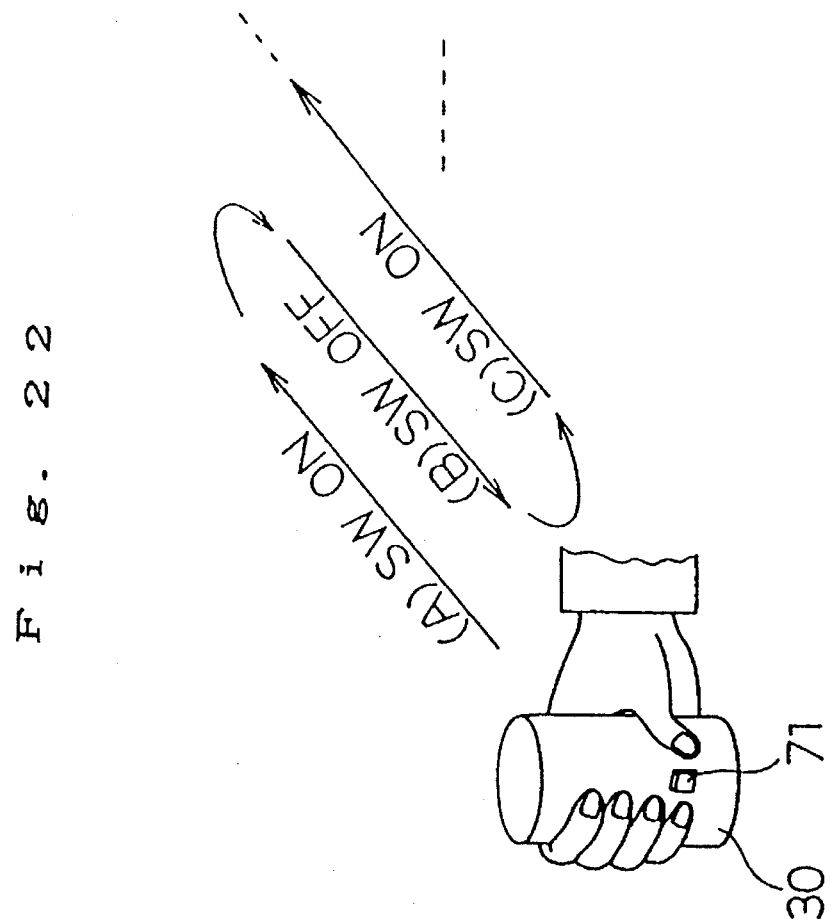
FIG. 22 is a perspective view showing an operational example of one embodiment of the present invention.

FIG. 22 is a perspective view to explain one embodiment of the operation according to the 17th aspect of the present invention, based on the similar consideration. The similar switch 71 can fix the position of the whole wrist. In FIG. 22, it is assumed that the whole wrist holding the device 30 carries out a reciprocating shift motion in turn in the directions of arrows (A), (B) and (C), which are the top right-hand direction in the paper and the reverse direction. At this time, when moving in the direction of the arrows (A) and (C), the switch 71 is turned OFF, and when moving in the direction of the arrow (B), the switch 71 is turned ON. Therefore, by setting that the change of the position and posture of the wrist is not input when the switch is ON, it is possible that only the shift in the direction of the arrows (A) and (C) is input. By repeating this operation, the designation of the position over the movable range of the arm becomes possible. Furthermore, by turning the switch 71 ON, there is no need to fix the arm at a specific position in the space, whereby fatigue of the arm can be prevented.

Figure 23:
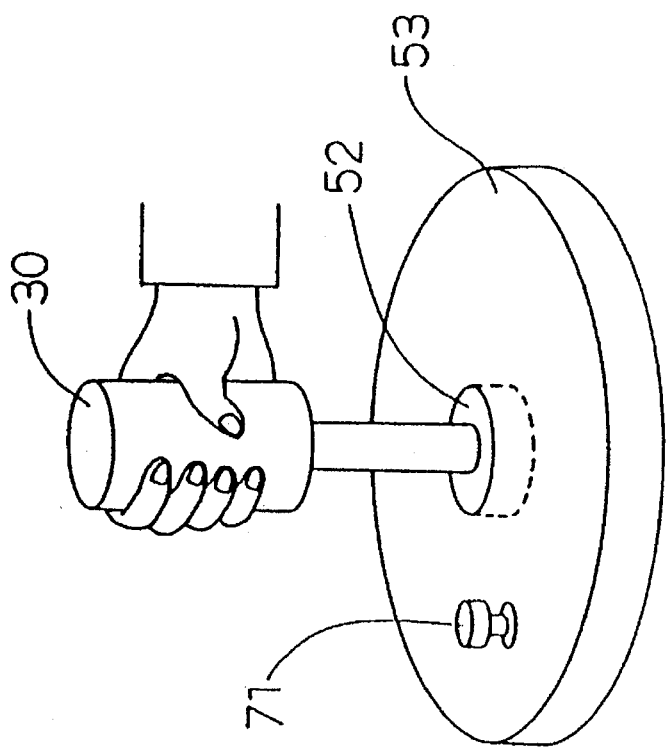
FIG. 23 is a perspective view showing the state of operating the device in one embodiment of the present invention.

FIG. 23 is a structural perspective view showing one embodiment according to the 18th aspect of the present invention. The basic structure is similar to that of FIG. 12 described as the embodiment according to the 11th aspect of the present invention. In FIG. 23, however, the shape of the device 30 is cylindrical, and a switch 71, which is the essential requirement in the 18th aspect of the present invention, is provided. Holding the device 30, the operator applies a force to the polyaxes sensor 52 (which is an auxiliary input means) by the whole wrist holding the device 30. The switch 71 can be operated by the other hand not holding the device 30. The information processing means 2 (not shown) can perform the functions described in the 16th or the 17th aspect of the present invention by the operation of the switch 71.

Incidentally, although only one switch is used in the description of the embodiments according to the 16th, 17th and 18th aspects of the present invention, respectively, switches correspond to each of them may be provided respectively, or only a switch corresponding to any one or two of these aspects of the present invention may be mounted.

Figure 24:
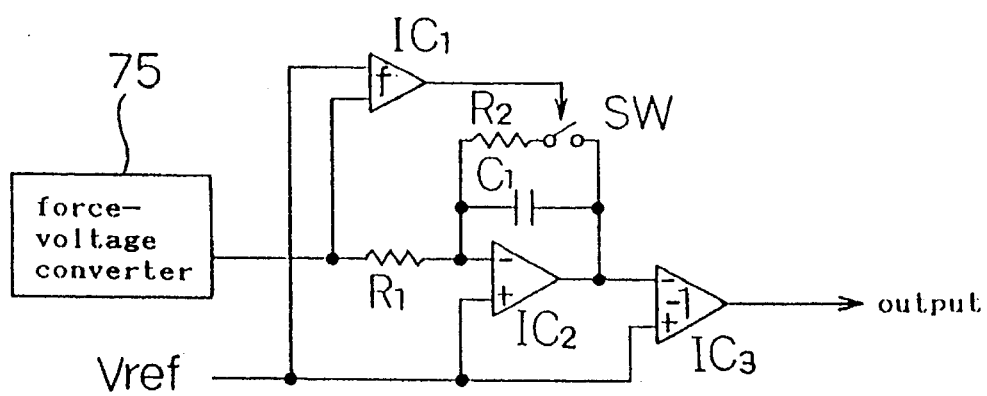
FIG. 24 is a signal processing circuit diagram in one embodiment of the present invention.
Figure 25:
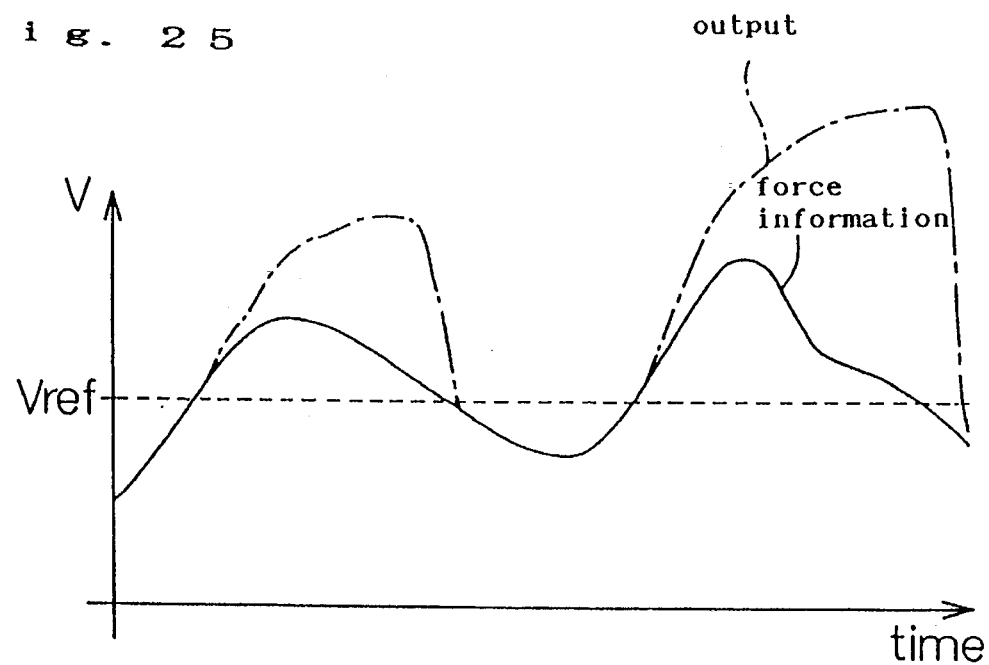
FIG. 25 is a waveform diagram showing one embodiment of the operation signal in FIG. 24.

FIG. 24 and FIG. 25 are the views for illustrating the 19th aspect of the present invention. FIG. 24 is a circuit block diagram for converting the force information to the positional information, such as bending of fingers, and FIG. 25 is a view of a waveform showing the operation results thereof. In FIG. 24, the force information converted to the voltage information by a force-voltage converter 75(pressure sensor output) is connected to the $IC_1$ circuit and the resistance $R_1$. The $IC_1$ circuit is a comparison circuit to compare the force information and the reference voltage Vref. When the force information is small, the switch SW is turned ON, and when it is large, the switch SW is turned OFF. When the switch SW is OFF, an inversion integral circuit is constituted by a resistance $R_1$, a capacitor $C_1$ and an $IC_2$ circuit to invert and integrate the force information and to input the inverted and integrated results to an $IC_3$ circuit. The $IC_3$ circuit is a differential circuit, and it inverts the voltage by making the reference voltage Vref as the standard to obtain uninverted integrated results. The reference voltage Vref is selected in the vicinity of the threshold for the determining if it is a large force or not. On the other hand, when the switch SW is ON, an inversion circuit is constituted by an $IC_2$ circuit, a resistance $R_1$ and a resistance $R_2$, and the inverted results are transmitted to the $IC_3$ circuit. Namely, the circuit in FIG. 24 carries out the integration when the force information is larger than the reference voltage, and when the force information is smaller than the reference voltage, it obtains the direct output. FIG. 25 shows the operation waveform. In the drawing, the force information is shown by a solid line, and the output is shown by a one dot chain line. When the force information as shown by the solid line of FIG. 25 is input, if the force information is smaller than the reference voltage Vref, the output is the same, and if it is larger than the reference voltage Vref, the integration action is carried out as shown by the one dot chain line. By using such means, there is no need to continue applying a big force necessary to turn ON. Thus, even if the force is loosened a little, the ON state can be maintained, and fatigue of the fingers can be prevented.

Figure 26:
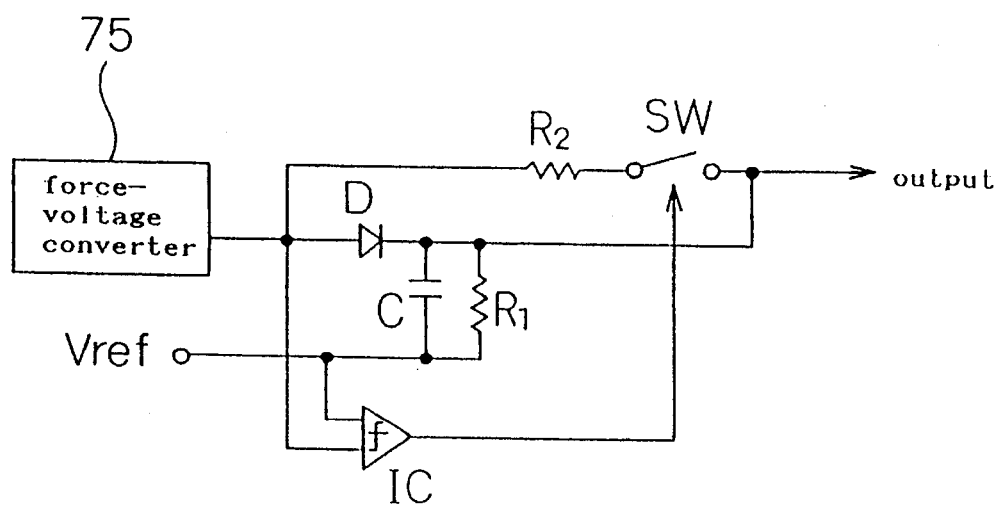
FIG. 26 is a signal processing circuit diagram in one embodiment of the present invention.
Figure 27:
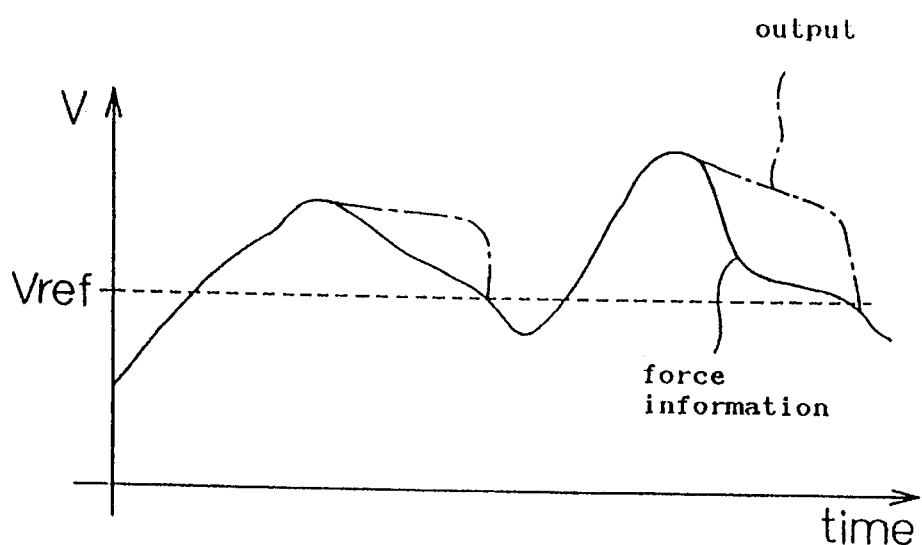
FIG. 27 is a waveform diagram showing one embodiment of the operation signal in FIG. 26.

FIG. 26 and FIG. 27 are the views for illustrating one embodiment according to the 20th aspect of the present invention. FIG. 26 is a circuit block diagram for converting the force information to the positional information, such as bending of the fingers, and FIG. 27 is a waveform diagram showing the operation results thereof. In FIG. 26, the force information converted to the voltage information by a force-voltage converter 75(pressure sensor output) is connected to an IC circuit, a diode D and a resistance $R_2$. The diode D, the capacitor C and the resistance $R_1$ constitute a maximum value-holding circuit (or peak hold circuit), and when the input voltage becomes low, it is held by the charge of the capacitor for a while. The charge of the capacitor is discharged slowly by the resistance $R_1$. The IC is a comparison circuit to compare the force information and the reference voltage Vref, and to control the opening/closing of the switch SW according to the results. The reference voltage is set similar to that in the 19th aspect of the present invention. When the force information is larger than the reference voltage Vref, the switch SW is turned OFF, and when it is smaller than the reference voltage, the switch SW is turned ON. When the switch SW is ON, the output voltage is connected via a resistance $R_2$ to the force information, therefore the output is substantially equal to the force information. Namely, the circuit of FIG. 26 carries out an operation to substantially hold the maximum value of the force information when the force information is larger than the reference voltage Vref, and when it is smaller than the reference voltage Vref, the circuit operates so that the output becomes substantially equal to the force information. FIG. 27 shows the operation waveform. In the drawing, the force information is shown by a solid line, and the output is shown by a one dot chain line. When the force information as shown by the solid line of FIG. 27 is input, if the force information is smaller than the reference voltage Vref, the output is the same, and if it is larger than the reference voltage Vref, the maximum value-holding operation is carried out. By using such means, there is no need to continue applying a big force, and fatigue of the fingers can be prevented.

Figure 28:
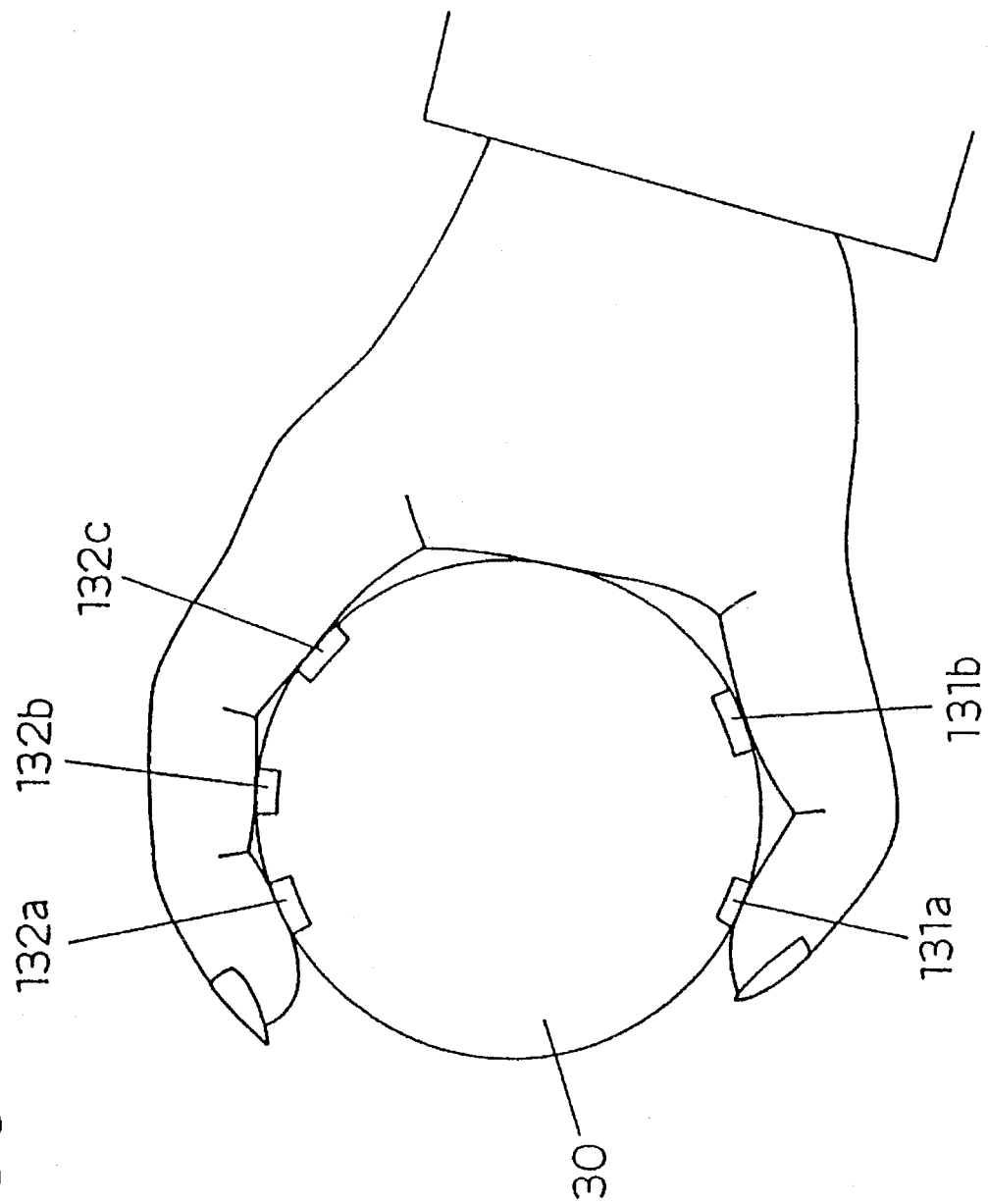
FIG. 28 is a perspective view showing the arrangement examples of the detecting means of a cylindrical device in one embodiment of the present invention.

FIG. 28 is a perspective view showing one embodiment according to the 21st aspect of the present invention. For the ease of presentation, the second finger and the third finger and the little finger are omitted, and the device 30 is held by the thumb and the first finger. Namely, in the situation holding the device 30, the portion of the tip joint of the thumb pushes the pressure sensor 131a, and the next portion pushes the pressure sensor 131b. Similarly, it is designed so that the first finger contacts with the pressure sensors 132a, 132b and 132c. Accordingly, the intention to bend the joint of the tip of the thumb is detected by the pressure sensor 131a, and the intention to bend the next joint of the thumb is detected by the pressure sensor 131b. Similarly, the intention to bend the joint of the tip of the first finger is detected by the pressure sensor 132a, and the intention to bend the next joint of the first finger is detected by the pressure sensor 132b. The intention to bend the joint closest to the palm can be detected by the pressure sensor 132c. Thus, the intention to bend each joint of all fingers toward the palm can be detected by the pressure sensors provided corresponding to the surface of the device 30. On the other hand, the intention to shift in the direction of the inner face of the palm, which is another degree of freedom of the finger, becomes the motion to the right and left direction with regard to the direction of the belly portion of the finger, whereby it can be detected by providing the pressure sensors 32b and 32c at the right and at the left of the direction of the belly portion of fingers as shown in FIG. 6.

FIG. 29(a) is a perspective view in the state of holding the device 30, and a partial sectional view is shown in FIG. 29(b), thus showing one embodiment according to the 22nd aspect of the present invention. In FIG. 29(a), both ends of a cylindrical device 30 being held are in the form of a semicylindrical shape having fringe portions which are connected by a screw 126. Namely, the sectional view of both ends is shown in FIG. 29(b). Furthermore, the part held by an actual hand is in the form of two semicylindrical shapes linked therewith. The connection thereof can be realized by, for example, linking the gap between the two semicylindrical shapes via an elastic body or an elastic plastic body 125. By fastening the screw 126, the diameter of the cylindrical shape becomes small, and by loosening the screw 126, the diameter of the cylindrical shape becomes large. Therefore, an operator who has large hands uses it by making its diameter large by loosening the screw for the ease of grasp, and a person who has small hands like a child uses it by making its diameter small by fastening the screw for the ease of grasp.

Figure 30A:
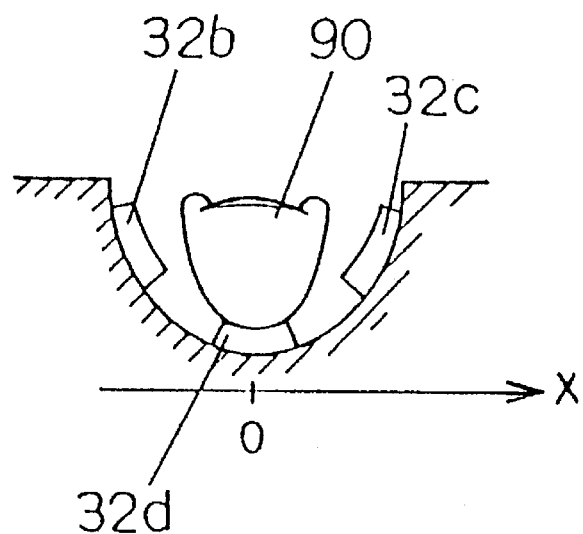
FIGS. 30(a) and 30(b) are sectional views showing the relation between the finger and the detector in one embodiment of the present invention.
Figure 30B:
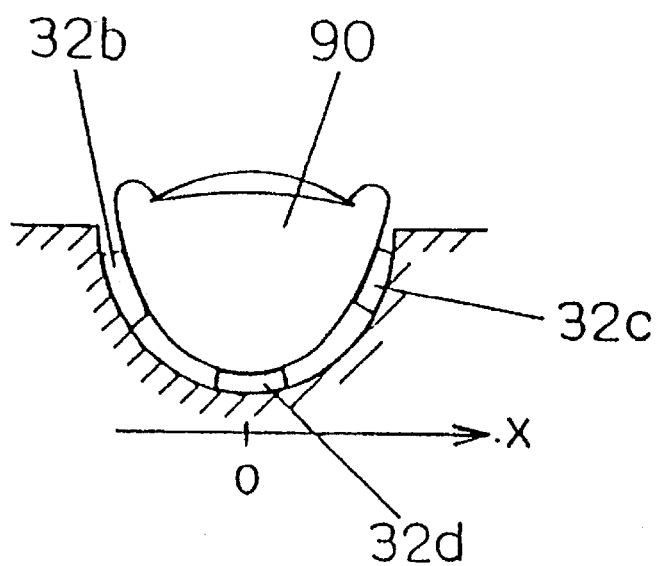

Next, one embodiment according to the 23rd aspect of the present invention will be described with reference to FIGS. 30(a), 30(b), FIGS. 31(a)–31(d) and FIG. 32. FIGS. 30(a)

and 30(b) are sectional views of a part of the device 30 similar to that of FIG. 7. FIG. 30(a) shows the situation where the finger 90 is small, and FIG. 30(b) shows the situation where the finger 90 is large. As shown in FIG. 30(a), when the finger 90 is small, there exists a state where a pressure is not applied to any of the pressure sensors 32b and 32c which detect the intention to move the finger to right and left. On the contrary, when the finger 90 is large as shown in FIG. 30(b), the situation is that a pressure is applied to both pressure sensors 32b and 32c.

Figure 31A:
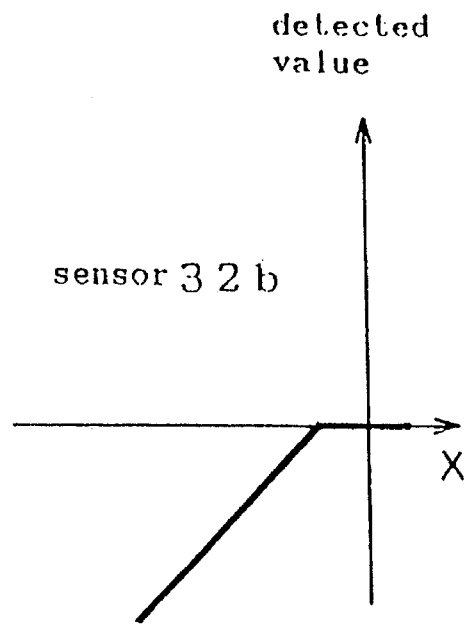
FIGS. 31(a)–31(d) are characteristic waveform diagrams showing one example of the detected results in FIGS. 30(a) and 30(b).
Figure 31B:
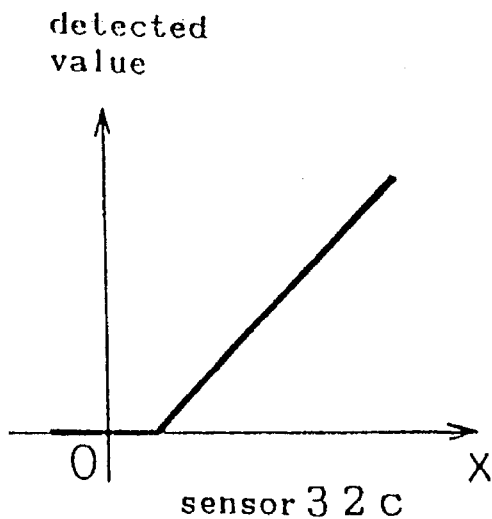
Figure 31C:
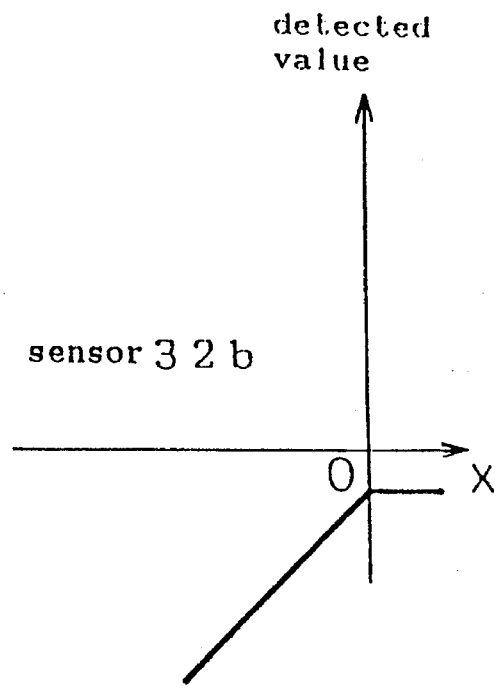
Figure 31D:
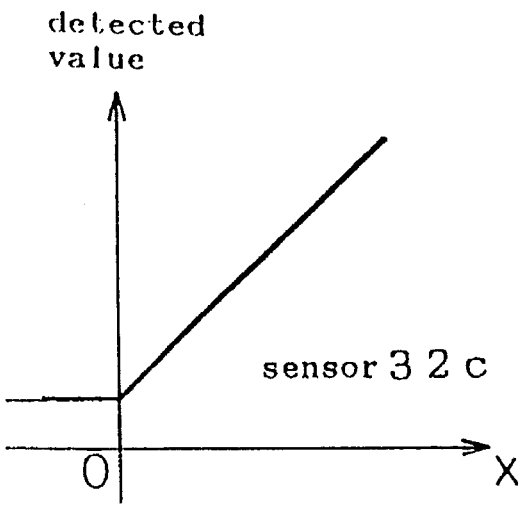

FIGS. 31(a) to 31(d) show the detected result of the pressure sensors 32b and 32c in the state of FIGS. 30(a) and 30(b), and the lateral axis x shows the magnitude of the force to bend the finger, taking a positive number to the right. As in FIG. 30(a), FIGS. 31(a) and 31(b) show a detected result in the case that the finger 90 is small, and FIGS. 31(c) and 31(d) show a detected result in the case that the finger 90 is large. As shown in FIGS. 31(a) and 31(b), if the finger 90 is small, there is a gap between the finger and the pressure sensors 32b and 32c, whereby when the force x is small, the sensor 32 cannot detect the force, and it is not until the force x becomes larger than x1 that the sensor 32 can detect the force. Similarly, when the force x is larger than x2 (the negative value), the sensor 32b cannot detect the force due to the gap, and it is not until the force x becomes smaller than x2 that the sensor 32b can detect the force. In FIGS. 31(c) and (d), since the finger 90 is large, a pressure is always applied to the pressure sensors 32b and 32c. Though the finger deforms itself more or less to match with the shape, a force f1 is always applied to the direction not applying a force. Therefore, the values detected by the pressure sensors 32b and 32c differ according to the size of the finger.

Figure 32:
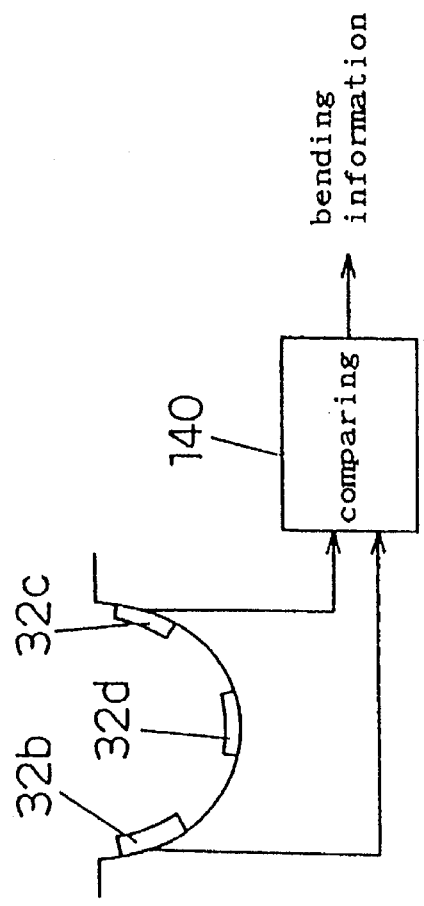
FIG. 32 is a signal processing circuit diagram in one embodiment of the present invention.

FIG. 32 is a circuit block diagram in order to avoid this influence. Namely, it obtains the bending information of a finger in the right and left directions by comparing the detected results by the pressure sensors 32b and 32c for detecting the intention to move the finger to right and left with a comparison means. When the finger is small and there is no intention to bend it to the right and left directions, the output of the two pressure sensors 32b and 32c are both 0, and even if they are compared by the comparison means 140, the value remains 0. On the other hand, when the finger is large and there is no intention to bend the finger, the output value of the two pressure sensors 32b and 32c are the same value, whereby the compared result by the comparison means 140 becomes 0. When there is an intention to bend the finger, any one of the two pressure sensors 32b and 32c receives a clearly larger force, whereby the outputs of the two sensors can be compared to make it the bending information of the finger. Namely, the intention to bend the finger to right and left can be obtained without regard to the size of the finger.

Figure 33:
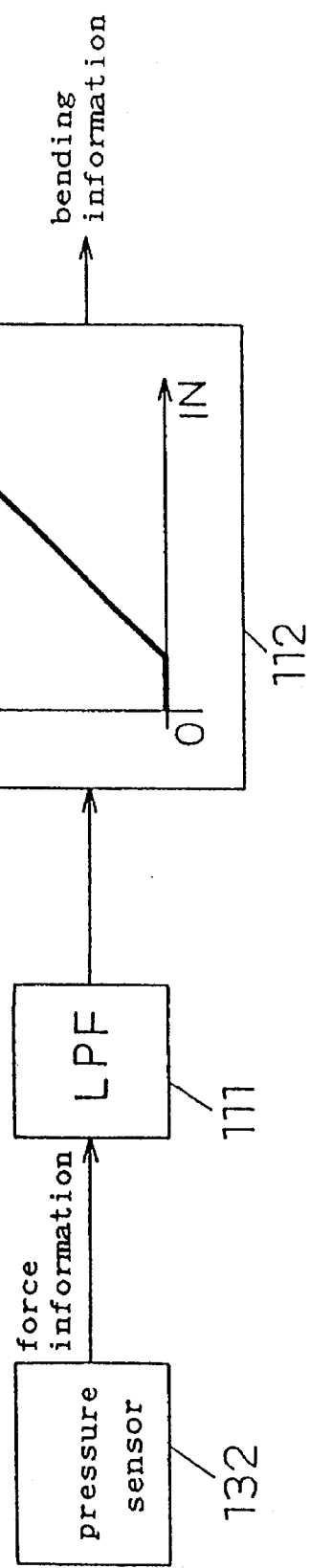
FIG. 33 is a signal processing circuit diagram in one embodiment of the present invention.

FIG. 33 shows one embodiment according to the 24th and 25th aspects of the present invention. As already described, the pressure sensor 132 which detects the intention to bend the finger also detects the trembles of fingers and unevenness of the force, when it detects the force to bend the finger. The intention information containing this unnecessary information is input to the low-pass filter 111. The low-pass filter 111 attenuates the component of rapid changes such as trembles. The information passed through the low-pass filter 111 is transmitted to the means for calculating the dead zone 112. The means for calculating the dead zone 112 carries out a process which does not react to a minute value. Thereby, the influences of the case where small forces are applied unconsciously, for example, a case where a finger is bent not related to an intention to bend the finger, the influence appears at the adjacent finger, and these influences can be removed. In FIG. 33, the description was made joining the 24th aspect and the 25th aspect of the present invention into one embodiment, it is needless to say that only the low-pass filter 111 or the means for calculating the dead zone 112 can obtain a certain effect. Incidentally, if the order of the low-pass filter 111 and the means for calculating the dead zone 112 is reversed, the average value of the output results of the means for calculating the dead zone 112 varies depending on the strength of the trembles of hands and the like, therefore it is not preferable.

Figure 34:
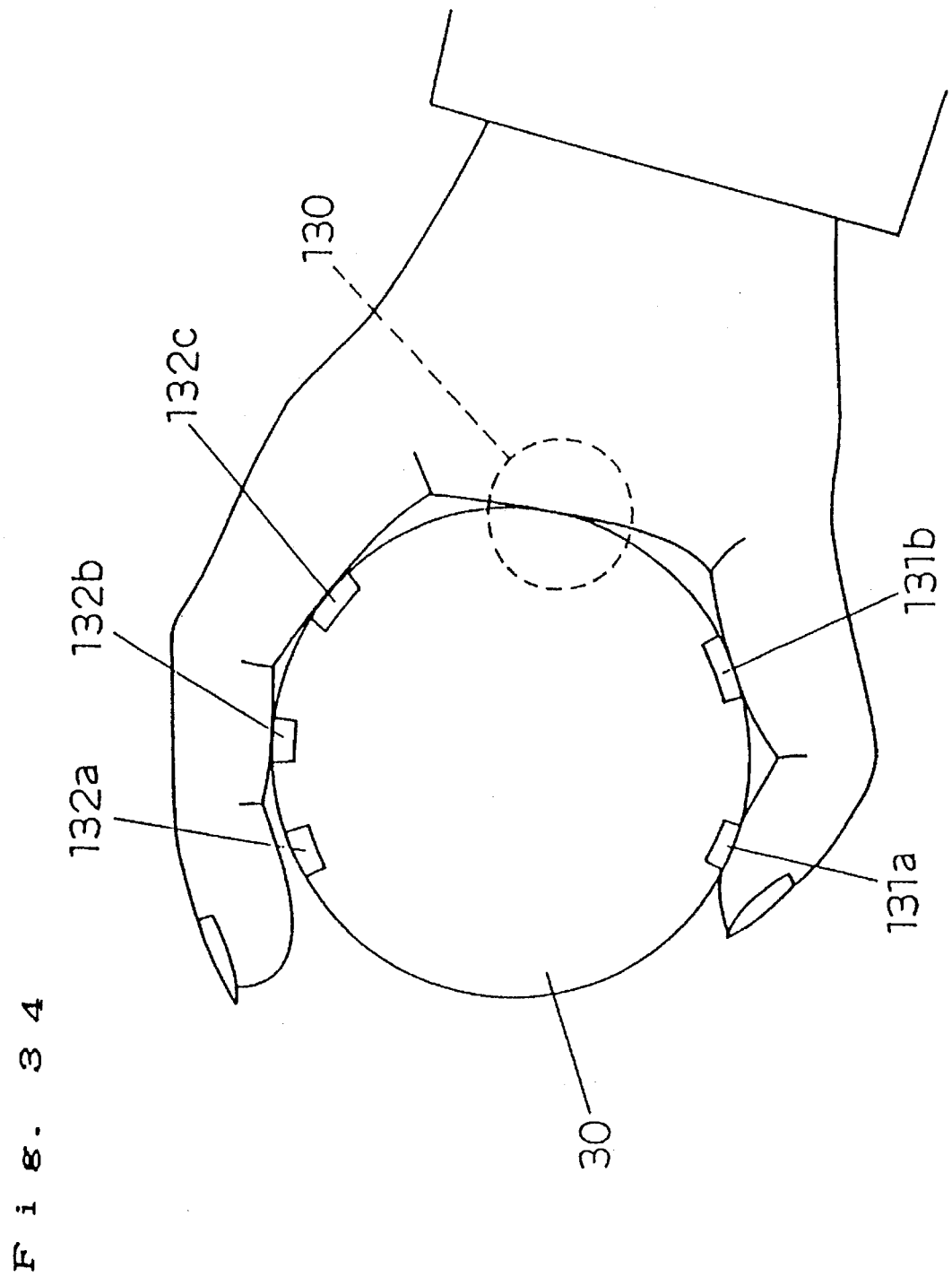
FIG. 34 is a perspective view showing the state of holding a cylindrical device in one embodiment of the present invention.
Figure 35:
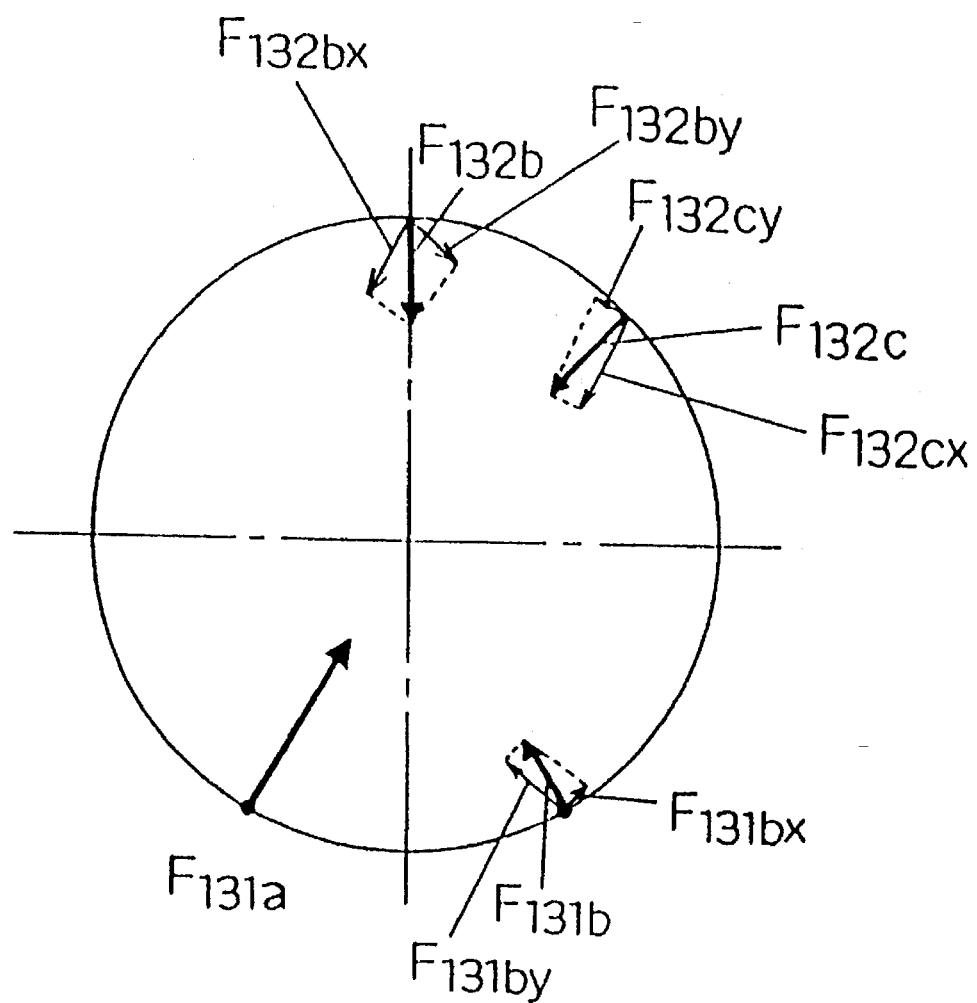
FIG. 35 is a view showing the relation with a force vector in a cylindrical device in one embodiment of the present invention.

FIG. 34 is a perspective view showing the state of holding the device 30, and showing the preconditions relating to the 26th and 27th aspects of the present invention which will be described now. The device 30 is cylindrical, and FIG. 34 is a sectional view of the part held by the thumb and the first finger. In FIG. 34, the intention to bend the tip joint of the thumb is detected by the pressure sensor 131a, and the intention to bend the next joint is detected by the pressure sensor 131b. Similarly, the intention to bend the tip joint of the first finger is detected by the pressure sensor 132a, the intention to bend the next joint is detected by the pressure sensor 132b, and the intention to bend the base joint is detected by the pressure sensor 132c. In FIG. 34, the state that a force is not applied to the pressure sensor 132a is shown. Furthermore, there is a case where a pressure is applied in the part between the thumb and the first finger in order to hold the device 30. FIG. 35 shows the magnitude of each pressure and the direction thereof in the state of holding the device 30. In FIG. 35, it is assumed that the force at the pressure sensor 131a is F131a, the force at the pressure sensor 131b is F131b, the force at the pressure sensor 132b is F132b, and the force at the pressure sensor 132c is F132c. Since the force at the pressure sensor 132a is zero, it does not appear in FIG. 35. Incidentally, the force at the part 130 between the thumb and the first finger is assumed to be zero, being regarded as the force for holding the device 30. In FIG. 35, all the four forces F131a, F131b, F132b, and F132c are the vector volume toward the origin of the cylinder. Since the device 30 is held and stopped, the composite vector (sum of the vectors) is zero. Namely, in FIG. 35, the force is analyzed in the direction of the force F131a and the component of the directions crossing at right angles therewith, F131bx, F131by, F132bx, F132by, F132cx and F132cy, and the sum of F131a, F131bx, F132bx and F132cx, and the sum of F131by, F132by and F132cy are zero, respectively.

If the force is increased to bend largely the tip of the thumb, the force F131a increases. Then, in order to hold stably the device 30, the forces of other fingers must be increased. At this time, however, other fingers do not apply the force with an intention. Therefore, the forces of other fingers cannot be larger than the force of the thumb, and must be small. That is, the small forces are regarded not to be connected with the intention to bend the finger.

Figure 36:
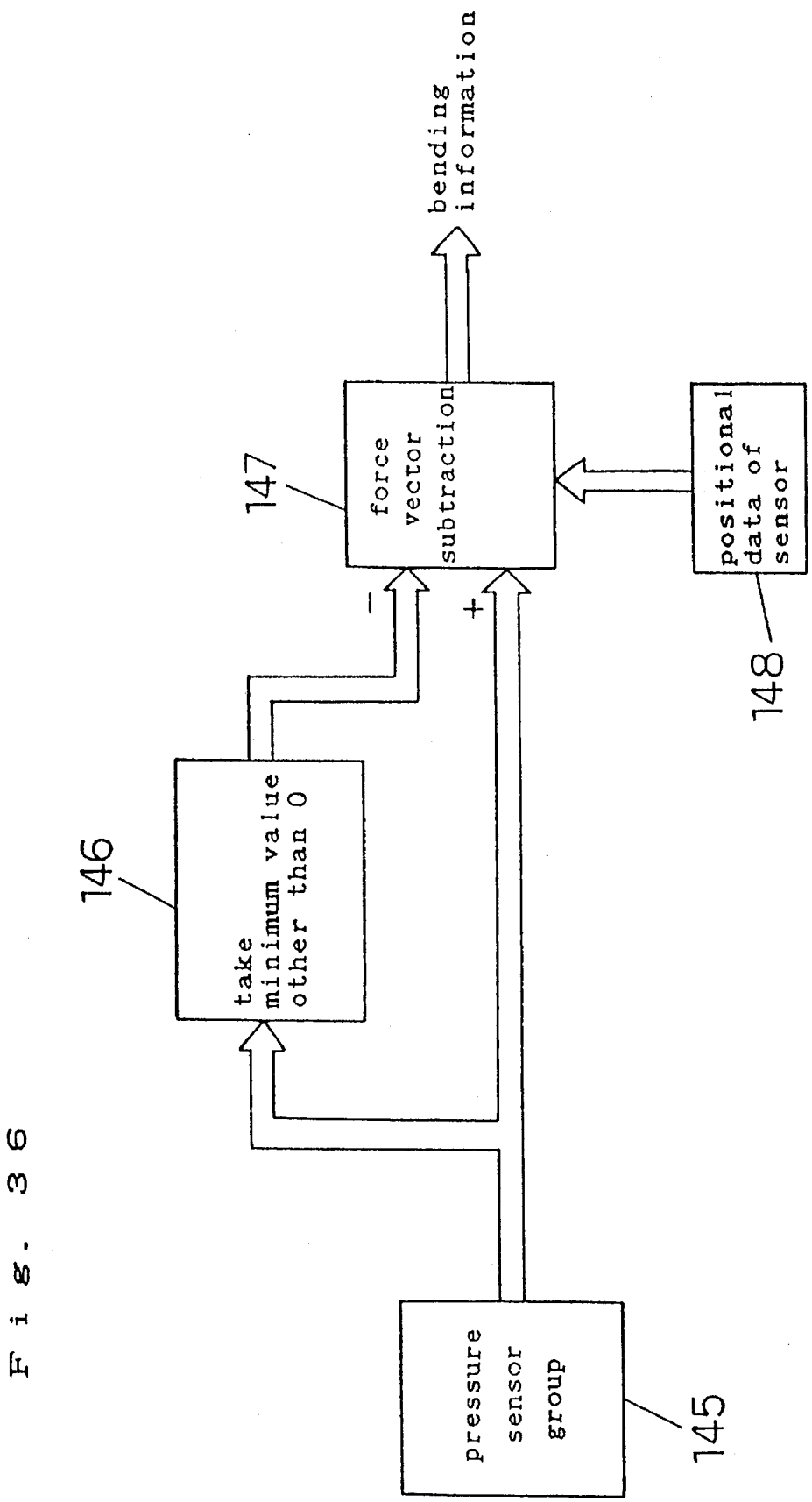
FIG. 36 is a signal processing circuit diagram in one embodiment of the present invention.

FIG. 36 is a circuit block diagram showing one embodiment according to the 26th aspect of the present invention. The information of the intention to bend each finger, containing the information to hold the device 30, detected by the pressure sensor group 145 comprising the pressure sensors 131a, 131b, 132a and 132b described in FIG. 34, are transmitted to the arithmetic means 146 for taking out the minimum value and the subtraction means 147. The arithmetic means 146 takes out the minimum force vector among the forces which are not zero, from the force information. The minimum force vector taken out is transmitted to the subtraction means 147. The subtraction means 147 subtracts the value of the minimum force vector from each force vector based on the positional data 148 of each sensor. The subtracted value is used as the bending information of the fingers. Incidentally, the output of the pressure sensor from which the minimum force vector is detected is made zero. Since the force vector which is relatively small is considered to have no relations with the intention to bend, it can be regarded to satisfy the holding conditions of the device 30. And by subtracting the value from each force vector, the value becomes approximate to that of the force vector necessary for the hold to be subtracted, and the subtracted information is close to the intention to bend the fingers.

Figure 37:
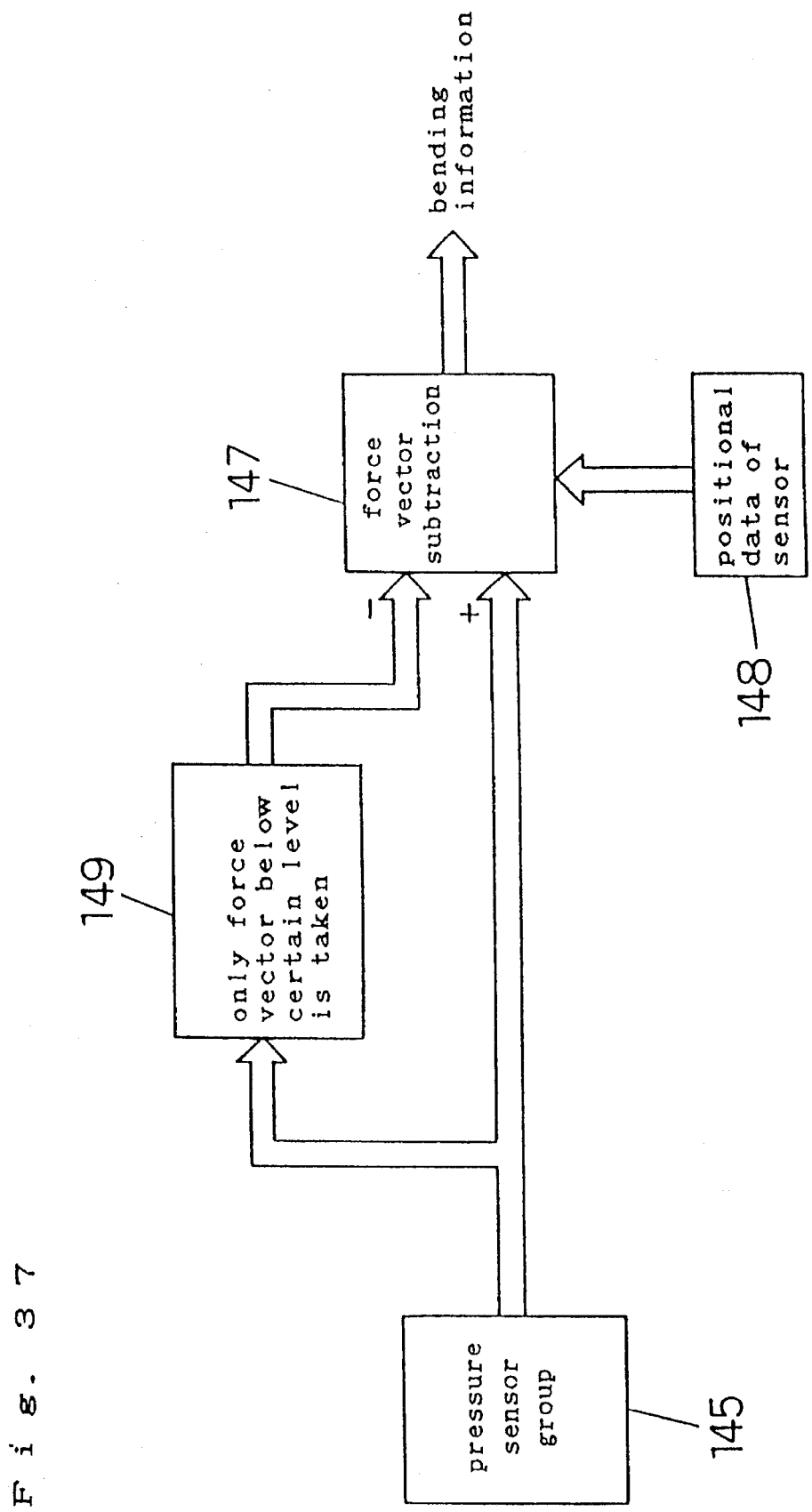
FIG. 37 is a signal processing circuit diagram in one embodiment of the present invention.

FIG. 37 is a circuit block diagram showing another embodiment according to the 26th aspect of the present invention. The detailed description of the part having the same structure with that of FIG. 36 is omitted. The information of the intention to bend each finger containing the information to hold the device 30, detected by the pressure sensor group 145, are transmitted to the arithmetic means 149 for taking out the force vector below a certain level and the subtraction means 147. At the arithmetic means 149, only the force vector below a certain level is taken out, and is transmitted to the force vector subtraction means 147. At the force vector subtraction means 147, as in the case of FIG. 36, the sum of the detected value of the force vector below a certain level is subtracted from the information detected by the pressure sensor group 145. The detected value is used as the bending information of the fingers. Incidentally, the output of the pressure sensor from which the force vector below a certain level is detected is made zero. As in the case of FIG. 36, since the force vector which is relatively small is considered to have no relation with the intention to bend, it can be regarded to satisfy the holding conditions of the device 30. And by subtracting the value from each force vector, the value becomes approximate to that of the force vector necessary for the hold being subtracted, and the subtracted information is close to the intention to bend the fingers.

Figure 38:
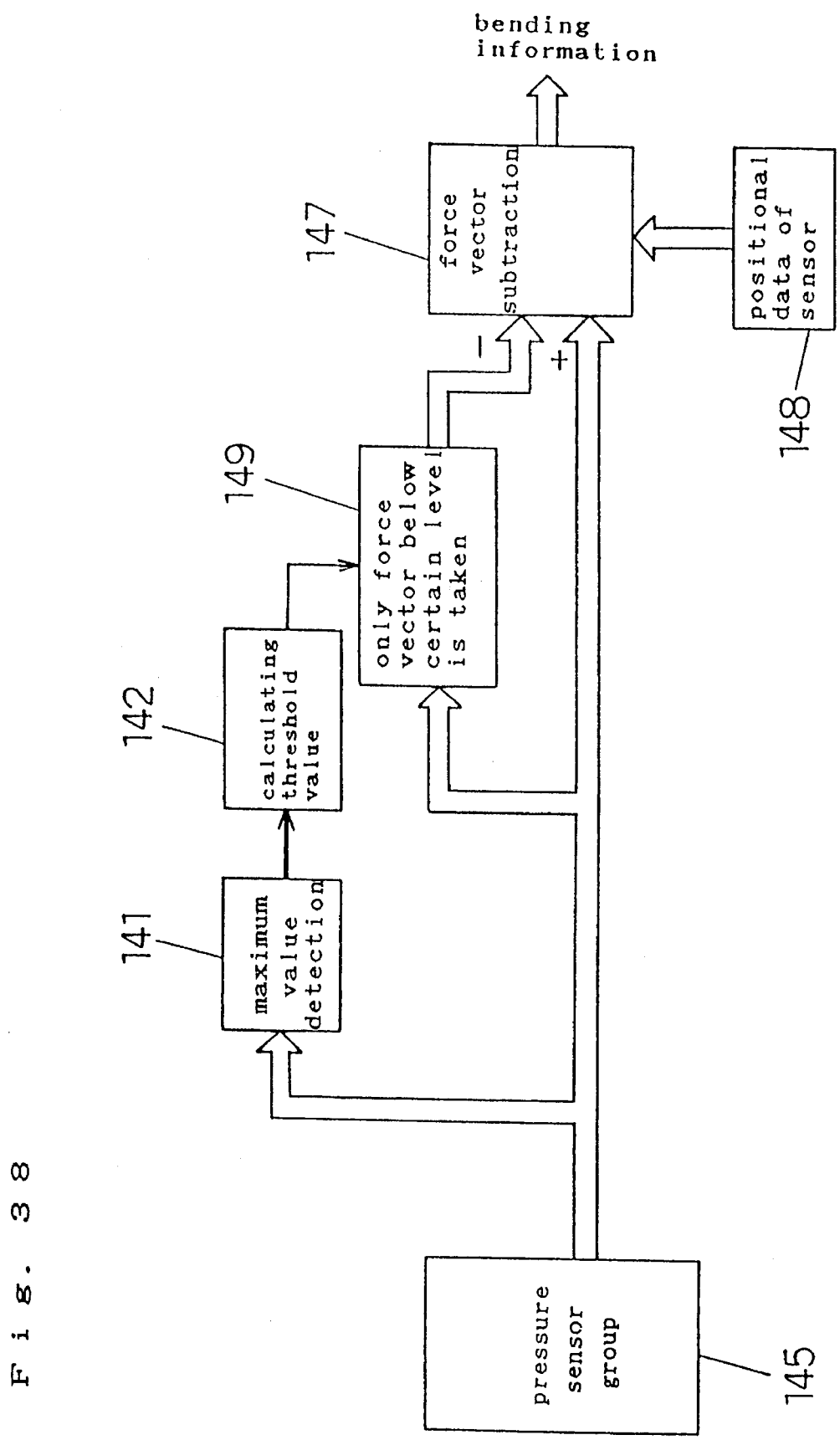
FIG. 38 is a signal processing circuit diagram in one embodiment of the present invention.

FIG. 38 is a circuit block diagram showing another embodiment according to the 26th aspect of the present invention. The detailed description of the part having the same structure with that of FIG. 37 is omitted. The information of the intention to bend each finger containing the information to hold the device 30, detected by the pressure sensor group 145, are transmitted to the maximum value-detecting means 141, the calculating means 149 for taking out the force vector below a certain level and the subtraction means 147. The maximum value-detecting means 141 calculates the maximum value of the input value. The obtained maximum value information is transmitted to the threshold calculating means 142. The result of the threshold calculating means 142 is transmitted to the arithmetic means 149. The threshold calculating means 142 obtains the threshold by, for example, multiplying the input value by a certain coefficient. At the arithmetic means 149, only the force vector below a certain threshold level determined by the threshold calculating means 142 is taken out, and is transmitted to the force vector subtraction means 147. At the force vector subtraction means 147, as in the case of FIG. 37, the value of the force vector below a certain threshold level taken out is subtracted from the information detected by the pressure sensor group 145. The subtracted value is used as the bending information of the fingers. As in the case of FIG. 37, since the force vector which is relatively small is considered to have no relation with the intention to bend, and the threshold value varies associating with the maximum value with the largest intention, it can be regarded to satisfy the holding conditions of the device 30 continuously.

Figure 39:
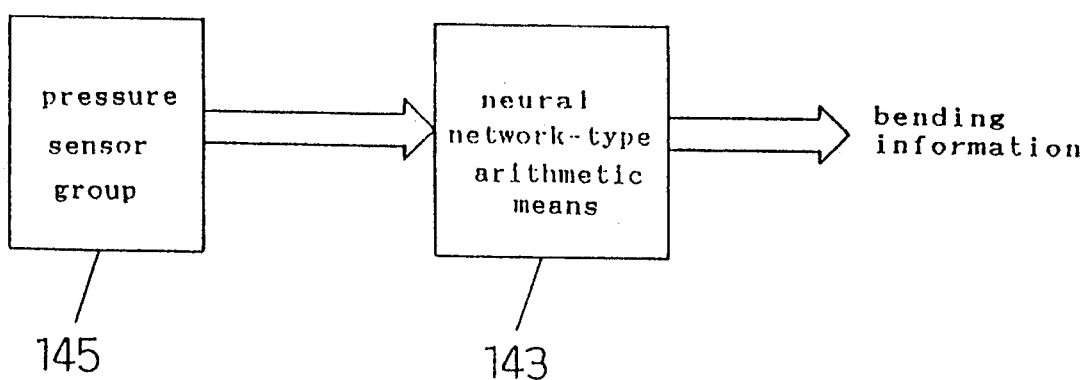
FIG. 39 is a signal processing circuit diagram in one embodiment of the present invention.
Figure 40:
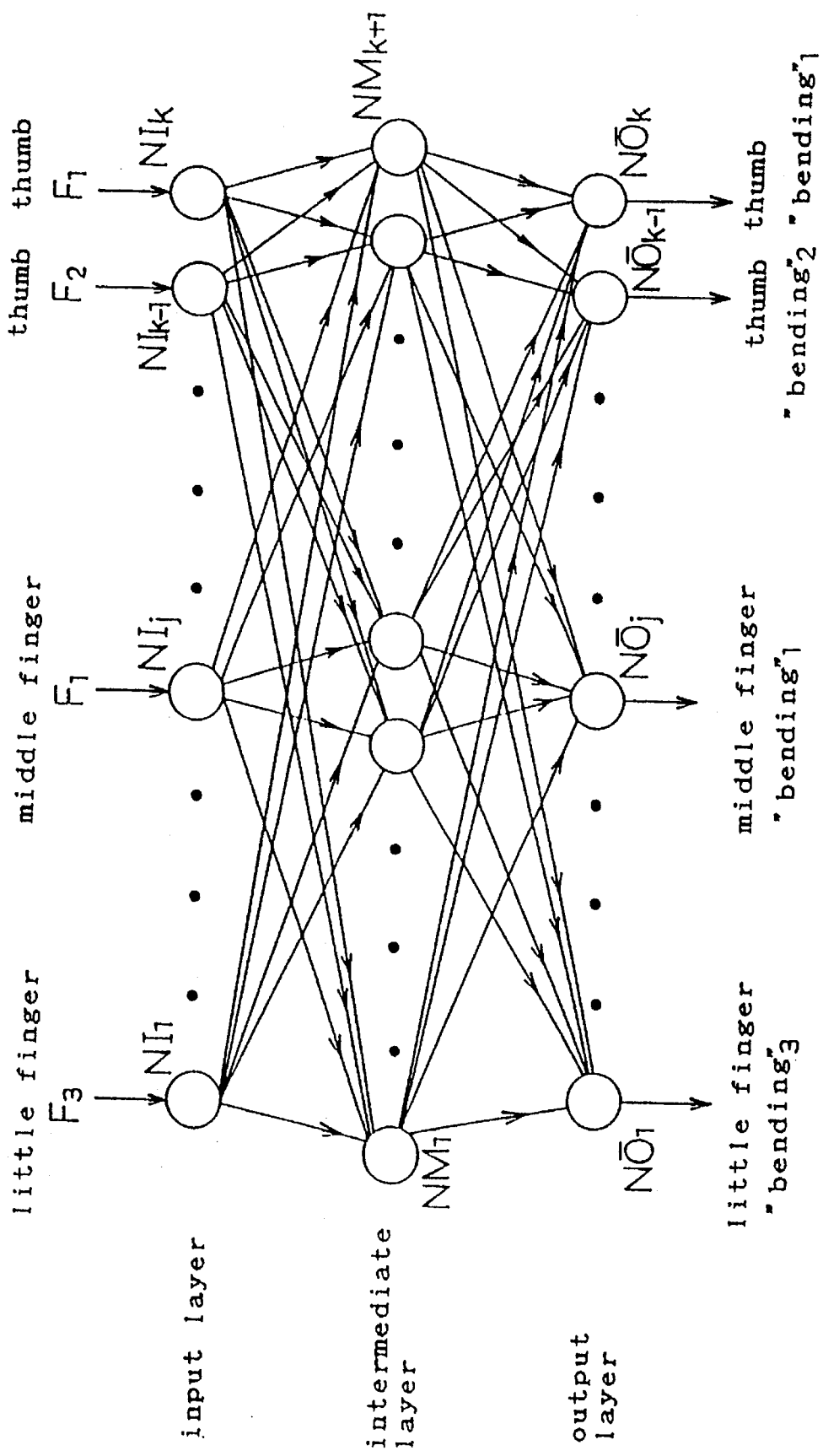
FIG. 40 is a circuit block diagram showing a structural example of a neural network in the signal processing circuit of one embodiment of the present invention.

FIG. 39 is a process block diagram showing the signal processing method in one embodiment according to the 27th aspect of the present invention. In FIG. 39, the information of the intention to bend containing the information for holding, detected by the pressure sensor group 145, are transmitted to the neural network-type arithmetic means 143, and only the information of the intention to bend the fingers are taken out as the bending information of the fingers. FIG. 40 shows the details of the neural network-type arithmetic means 143, and comprises a neural cell (or neuron) group having three layers, input layers, intermediate layers and output layers, and a force information to bend the joint of each finger is input to each neural cell (or neuron) $(NI_1, NI_2, \ldots NI_k)$ of the input layer. Each neural cell (or neuron) gives a certain weight to the input information to determine the output by the threshold logic signal processing (sgn function) or the corresponding signal processing (sigmoid function, and the like). The weight is preliminarily determined by a prior study. The output information of the neural cell (or neuron) in the input layer is transmitted to each neural cell (or neuron) in the intermediate layer $(NM_1, NM_2, \ldots NM_{k+i})$. Each neural cell (or neuron) in the intermediate layer gives and adds a certain weight to the output information of each neural cell (or neuron), and carries out the signal processing similar to that of the neural cell (or neuron) in the input cell. The weight is preliminarily determined by a prior study. Each output information of the neural cell (or neuron) in the intermediate layer is transmitted to each neural cell (or neuron) in the output layer $(NO_1, NO_2, \ldots NO_k)$. The neural cell (or neuron) in the output layer gives and adds a certain weight to the output of the neural cell (or neuron) in the intermediate layer. The added results are used as the bending information of the joint of each finger.

The method of prior study of the weight at the time of input to each neural cell (or neuron) in FIG. 40 will now be described. The study is carried out so that the error among the result calculated by the neural network, the data of angles to be bent and the force data given by the actual finger becomes minimum. As the study method, a back propagation method is well known. (For example, Rumelhart, D. E., McGlelland, J. L. and the PDP Research Group: Parallel Distributed Processing: Explorations in the Micro-structure of Cognition, Vol. 1, pp.318–362, MIT Press (1986).) By this study, the weight of the input phase of each neural cell (or neuron) is determined. Thereby, from the information of the intention to bend the fingers containing the information to hold the device 30, only the information of the intention to bend the fingers are taken out, whereby the data input has higher accuracy. Namely, since the relation between the intention to bend the fingers and the force while holding the device has been preliminarily identified as the neural network, by inputting the detected result to the neural network, the information of the intention to bend the fingers can be taken out as an output.

Incidentally, the 27th aspect of the present invention was described by using a three layered neural network-type arithmetic means, but it is obvious that other methods of neural network-type arithmetic means may be used.

Figure 41:
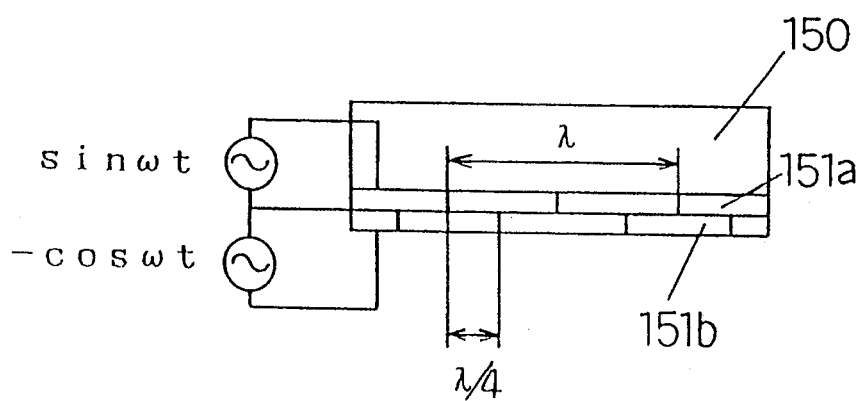
FIG. 41 is a structural block diagram showing the operational principle of the ultrasonic vibration motor in one embodiment of the present invention.

FIGS. 41, 42, 43 and 44 are views illustrating briefly the principles of the ultrasonic vibration motor used in the 28th, 29th and 30th aspects of the present invention. Please refer to the detailed description included in "Kawasaki, et al, U.S. Pat. No. 4,853,579. FIG. 41 shows the basic structure of the ultrasonic vibration motor, in which an elastic body 150 is stuck on the two-layered piezoelectric ceramics 151a and 151b. The two-layered piezoelectric ceramics 151a and 151*b* are polarized so that the polarized directions are alternated per the (λ/2) section, and stuck so that the phase of the two layers is shifted by (λ/4). When the alternating signal in which the phase is shifted by 90 degrees with each other in the resonant frequency is applied to these two-layered piezoelectric ceramics 151*a* and 151*b*, the deformation shown in FIG. 42 is caused. FIG. 42 shows the deformation including the elastic body 150 in the time series, and with the lapse of time, the deformation varies in the order of (*a*), (*b*), (*c*), (*d*) and (*e*) of FIG. 42. Furthermore, (*e*) is identical with (*a*), and repeats (*b*), (*c*), and so on. Overall wave motion shifts from the left to the right. Seeing the behavior at one point in the elastic body in each time, it is understood that it draws the elliptical orbit rotating counterclockwise as shown in FIG. 43. In this situation, it is FIG. 44 that shows the situation in which a moving body 155 is placed on the elastic body 150. In FIG. 44, at the point where the elastic body 150 contacts with the moving body 155, the contact portion carries out an elliptical motion rotating counterclockwise, and the elastic body moves to left at the contact point. Therefore, a force in the left direction is generated to the moving body 155, and if the moving body 155 overcomes the static friction, it starts to move to the left direction. Thus, it becomes possible for the ultrasonic vibration motor to shift or give force to the optional object placed on the elastic body 150.

FIG. 45 shows one embodiment according to the 28th, 29th and 30th aspects of the present invention using the ultrasonic vibration motor. In FIG. 45, when a finger is put on the device 30, an ultrasonic vibration motor 156 is provided to the place where the belly portion of the finger contacts, below which a pressure sensor 32 for detecting the pressure in the vertical direction is provided. The detected results by the pressure sensor 32 are input to the reciprocal arithmetic means 157 to obtain the reciprocal value of the pressure. The obtained reciprocal value of the pressure is input to the multiplying means 158 to multiply it by the force objective value. The multiplied results are transmitted to the drive circuit 159, and drives the ultrasonic vibration motor 156. The ultrasonic vibration motor 156 generates a force Fx in the face where the belly portion of the finger contacts by the drive circuit 159. The belly portion of the finger can sense the repulsive force in the horizontal direction by this force Fx. The force Fx given to the finger from the ultrasonic vibration motor 156 varies depending on whether the finger pushes strongly or not. Namely, the stronger the finger pushes the face of the elastic body of the ultrasonic vibration motor 156, the larger force can be obtained. Therefore, even if the same drive instruction is given, if the pushing force of the finger is large, a large repulsive force can be obtained, and if the pushing force of the finger is small, only a small repulsive force can be obtained. Since the pushing force can be detected by the pressure sensor 32, by getting the reciprocal and multiplying it by the objective value of the repulsive force, the influences by the pushing force can be canceled, and the repulsive force along the objective value can be obtained.

On the other hand, the information of the force by which the surface of the finger opposes against the generated repulsive force is a load of the ultrasonic vibration motor 156, whereby it can be calculated from the electric current of the drive circuit 159. However, as described above, since the ultrasonic vibration motor 156 is driven by the alternating current, the current is calculated as an average current by the average current detecting means 160.

Incidentally, in the 29th and 30th aspect of the present invention, the explanation was made by using an ultrasonic vibration motor using piezoelectric ceramics, but as with the means to generate the oscillatory wave, it is needless to say that it is not limited to piezoelectric ceramics, and a magnetic body and the like can cause similar effects.

In the above embodiments, the explanation was made by taking an example in which the force sensation exhibiting device for hands or the data input device for hands and the information processing means are connected via a cable, but it is also possible to realize the information communication by means of a radio wave or light, by mounting the supply source in the force sensation exhibiting device for hands or the data input device for hands.

As is obvious from the above description, the above-mentioned respective inventions can be used extremely easily by a simple action of "grasping" without mounting a glove and the like Furthermore, according to the 1st, 2nd, 3rd and 13th aspects of the present invention, the repulsive force which the palm receives when operating an object, e.g. in the case of holding a virtual object, can be exhibited by a relatively easy method. And the 4th and 5th aspects of the present invention utilize the pressure at the tip of the finger, and the data input operation to the information processing means is made simple in the case where similar skillful action is necessary. In the 6th, 7th, 8th and 14th aspects of the present invention, the data input operation to the information processing means based on the skillful action can be made simple, by making it possible to give a repulsive force or the feeling of the repulsive force to the fingers when grasping a virtual object. The 9th, 10th and 11th aspects of the present invention make it possible to input the data of substantially infinite distance, and the 12th aspect of the present invention makes the grasp easy. The 16th, 17th and 18th aspects of the present invention make it possible to interrupt the operation easily, or input a wide range of positions without taking unreasonable postures. And the 19th and 20th aspects of the present invention eliminate the need for the fingers to apply a force continuously, and fatigue of the fingers is decreased.

Furthermore, according to the 21st aspect of the present invention, the intention corresponding to the bending of each joint of fingers can be detected by the detecting means corresponding to the bending of each joint, whereby operations which require complex motions of fingers become possible. The 22nd and 23rd aspects of the present invention make it possible to correspond to persons having different palm sizes, or different thickness or size of fingers, whereby the same device can be used from children to adults. The 24th and 25th aspects of the present invention can remove trembles of the fingers, fine variations such as unevenness of the force, and faint force, to smooth the actions of virtual fingers or fingers in a remote area. The 26th and 27th aspects of the present invention remove the influences of the force relating to the holding of the device but not relating to the intention to bend the fingers, and can take out only the information relating to the intention to input complex actions of the fingers. In the 28th and 29th aspects of the present invention, it becomes possible to generate a force in the direction of the inner surface of the finger, and also to generate a repulsive force against the direction thereof. The 30th aspect of the present invention can detect a force given by a finger to the inner direction of the belly portion of the finger to input complex actions of the fingers.

What is claimed is:

1. A data input device, comprising:

a housing which can be grasped by a hand, wherein the housing is equipped with a detecting means for detecting a displacement or a pressure at a portion of the housing on which fingers are placed at a time of the grasping by the hand, wherein the detecting means provides input data, and the data input device includes a means for determining an integral value or an incomplete integral value of a force detected by the detecting means, wherein the input data is optionally based on the integral value or the incomplete integral value of the force detected by the detecting means.

2. A data input device according to claim 1, wherein the integral value or the incomplete integral value is utilized when a value of the force detected by the detecting means exceeds a predetermined value, and when the value of the force detected by the detecting means is below the predetermined value, the input data is based on the value of the force detected by the detecting means.

3. A data input device according to claim 1, further including an auxiliary input means for inputting information relating to a position and posture of whole fingers.

4. A data input device according to claim 3, wherein the auxiliary input means includes plural axes force detecting means.

5. A data input device according to claim 3, wherein the auxiliary input means and the housing of the data input device are mounted on a common base.

6. A data input device according to claim 5, wherein the housing of the data input device and the auxiliary input means are disposed on the common base such that they are operated by separate hands of one operator.

7. A data input device according to claim 3, wherein the auxiliary input means includes an arm portion and a polyaxes force sensor section, wherein the housing of the data input device is connected to a first end of the arm portion and the polyaxes force sensor section is connected to a second end of the arm portion, such that when an operation is performed to change a position of the data input device, a force corresponding to the operation is applied to the polyaxes force sensor section.

8. A data input device according to claim 1, wherein the housing of the data input device is substantially cylindrical shaped.

9. A data input device according to claim 1, further including a manipulator, wherein the housing of the data input device is mounted at a tip of the manipulator, such that a position and posture of the data input device is movable with plural degrees of freedom.

10. A data input device according to claim 9, further including a repulsive force generator to generate a repulsive force in the data input device.

11. A data input device according to claim 1, wherein the housing of the data input device is substantially cylindrical shaped, and a diameter-adjusting means is provided on the housing for adjusting a size of a diameter of the housing.

12. A data input device according to claim 11, wherein the diameter-adjusting means is provided at a portion of the housing which does not contact the hand when the housing is grasped by the hand.

13. A data input device according to claim 11, wherein the diameter-adjusting means is provided at an outer side of the housing, between a thumb and a little finger when the housing is grasped.

14. A data input device according to claim 11, wherein the substantially cylindrical shaped housing is made from two half cylinders having an elastic body therebetween.

15. A data input device, comprising:

a housing which can be grasped by a hand, wherein the housing is equipped with a detecting means for detecting a displacement or a pressure at a portion of the housing on which fingers are placed at a time of the grasping by the hand, wherein the detecting means detects a value of a force applied by the fingers and provides input data, and means for determining a maximum value of the force detected by the detecting means, wherein the input data is optionally provided utilizing the maximum value of the force detected by the detecting means for a predetermined period, wherein the maximum value is held by a maximum value-holding circuit.

16. A data input device according to claim 15, wherein when the value of the force detected by the detecting means exceeds a predetermined value, the maximum value is used to provide the input data, and when the value of the force detected by the detecting means is below the predetermined value, the input data is based on the value of the force detected by the detecting means.

17. A data input device, comprising:

a housing which can be grasped by a hand, and plural detecting means for detecting a displacement or a pressure, wherein plural detecting means are provided in association with respective parts of the housing with which each finger belly portion to be detected contacts when the housing is grasped, such that the displacement or pressure from each finger belly portion to be detected is detected by plural detecting means, wherein the data input device determines a value which corresponds to a difference between detected values of two detecting means among the plural detecting means.

18. A data input device, comprising:

a housing which can be grasped by a hand., wherein the housing is equipped with a detecting means for detecting a displacement or a pressure at a portion of the housing on which fingers are placed at a time of the grasping of the housing by the hand, wherein the detecting means provides input data; and means for calculating a dead zone, wherein the means for calculating the dead zone determines that there is no input when the detected displacement or pressure is below a predetermined value, and wherein a value passed through said means for calculating the dead zone is the input data.

19. A data input device, comprising:

a housing which can be grasped by a hand, detecting means for detecting a displacement or a pressure provided at a portion of the housing on which fingers are placed when the housing is grasped, a low-pass filter through which the detected displacement or the pressure is made to pass to filter rapid changes in the detected displacement or pressure, and means for calculating a dead zone, wherein the means for calculating the dead zone determines that there is no input when the displacement or the pressure passed through the filter is below a predetermined value, wherein a value passed through the means for calculating the dead zone is determined to be an input value.

20. A data input device, comprising:

a housing which can be grasped by a hand, wherein the housing is equipped with plural detecting means, wherein each detecting means detects a displacement or a pressure at a respective portion of the housing on which a respective finger belly portion between two joints of a finger is placed at a time of the grasping of the housing by the hand, wherein each detecting means detects a resulting value corresponding to the detected displacement or pressure at the respective detecting means; and means for subtracting which subtracts the resulting value which is a minimum, but not zero, among the resulting values detected by the plural detecting means, wherein the means for subtracting subtracts the minimum resulting value from the respective resulting values to provide a subtracted value, and the subtracted value is provided as input data.

* * * * *